United States Patent [19]

Doria et al.

[11] Patent Number: 5,424,308
[45] Date of Patent: * Jun. 13, 1995

[54] CONDENSED PYRAZOLE 3-OXO-PROPANENITRILE DERIVATIVES

[75] Inventors: Gianfederico Doria, Milan; Anna M. Isetta, Rho; Mario Ferrari, Milan; Domenico Trizio, Cassina Rizzardi, all of Italy

[73] Assignee: Farmitalia Carlo Erba S.r.l., Milan, Italy

[ * ] Notice: The portion of the term of this patent subsequent to Jun. 13, 2009 has been disclaimed.

[21] Appl. No.: 635,157

[22] PCT Filed: Jun. 16, 1989

[86] PCT No.: PCT/EP89/00682

§ 371 Date: Feb. 24, 1994

§ 102(e) Date: Feb. 24, 1994

[87] PCT Pub. No.: WO89/12630

PCT Pub. Date: Dec. 28, 1989

[30] Foreign Application Priority Data

Jun. 20, 1988 [GB] United Kingdom ............... 8814587

[51] Int. Cl.⁶ ............... A61K 31/415; C07D 231/54; C07D 495/04
[52] U.S. Cl. ............... 514/232.8; 514/253; 514/322; 514/338; 514/403; 544/140; 544/371; 546/199; 546/271; 548/359.1; 548/359.5
[58] Field of Search ............... 548/359.1, 359.5; 514/403

[56] References Cited

U.S. PATENT DOCUMENTS

| | | |
|---|---|---|
| 2,989,538 | 6/1961 | Flores et al. . |
| 3,004,983 | 10/1961 | Loev et al. . |
| 4,140,785 | 2/1979 | Hoffman et al. . |
| 4,420,476 | 12/1983 | Philipp et al. . |
| 4,431,657 | 2/1984 | Philipp et al. . |
| 4,816,467 | 3/1989 | Doria et al. ............ 548/359.1 |
| 5,206,258 | 4/1993 | Doria et al. ............ 548/359.1 |

FOREIGN PATENT DOCUMENTS

| | | |
|---|---|---|
| 0005357 | 11/1979 | European Pat. Off. . |
| 0015156 | 9/1980 | European Pat. Off. . |
| 0286346 | 10/1988 | European Pat. Off. . |

*Primary Examiner*—Robert W. Ramsuer
*Attorney, Agent, or Firm*—Nikaido, Marmelstein, Murray & Cram

[57] ABSTRACT

Condensed pyrazole 3-oxo-propanenitrile derivatives of formula (I)

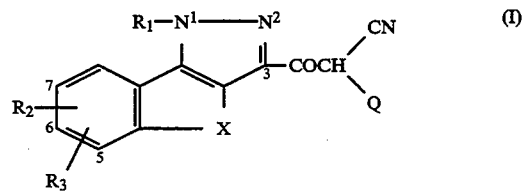

wherein X represents a —CH($R_4$)— group, an oxygen atom or a —S(O)$_n$— group where n is 0, 1 or 2; $R_1$ represents $C_1$-$C_6$ alkyl, pyridyl or unsubstituted or substituted phenyl; $R_2$, $R_3$ and $R_4$ are as defined herein; and Q represents hydrogen, carboxy, $C_2$-$C_7$ alkoxycarbonyl or a —CON($R_a$)$R_b$ group, $R_a$ and $R_b$ being as defined herein; and their pharmaceutically acceptable salts have immunomodulating activity and can be used in particular as immunomodulating agents, e.g. in the treatment of acute and chronic infections of both bacterial and viral origin, alone or in association with antibiotic agents, and in the treatment of neoplastic diseases, alone or in association with antitumoral agents, in mammals.

6 Claims, No Drawings

CONDENSED PYRAZOLE 3-OXO-PROPANENITRILE DERIVATIVES

The present invention relates to condensed pyrazole 3-oxo-propanenitrile derivatives, to a process for their preparation and to pharmaceutical compositions containing them.

The compounds of the invention have the general formula (I)

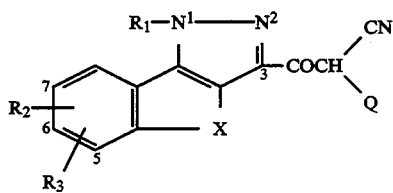

wherein
X represents:
a)

group wherein $R_4$ is hydrogen, $C_1$-$C_6$ alkyl or a

group wherein each of R' and R" independently is $C_1$-$C_6$ alkyl or R' and R", taken together with the nitrogen atom to which they are linked, form a heterocyclic ring which is selected from N-pyrrolidinyl, N-piperazinyl, hexahydroazepin-1-yl, thiomorpholino, morpholino and piperidino and which is unsubstituted or substituted by $C_1$-$C_6$ alkyl; or b) an oxygen atom or a —S(O)$_n$—group, wherein n is zero, 1 or 2;

$R_1$ represents $C_1$-$C_6$ alkyl, pyridyl or phenyl, the phenyl being unsubstituted or substituted by one or two substituents chosen independently from halogen, trifluoromethyl, $C_1$-$C_6$ alkyl, $C_1$-$C_6$ alkoxy, nitro, amino, formylamino and $C_2$-$C_8$ alkanoylamino; each of $R_2$ and $R_3$ is independently:

a') hydrogen, halogen, $C_1$-$C_6$ alkyl or trifluoromethyl;

b') hydroxy, $C_1$-$C_6$ alkoxy or $C_3$ or $C_4$ alkenyloxy;

c') nitro, amino, formylamino or $C_2$-$C_8$ alkanoylamino;

d') di($C_1$-$C_6$ alkyl)amino or a

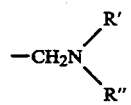

wherein R' and R" are as defined above;

e') $CH_2OH$, CHO, COOH or $C_2$-$C_7$ alkoxycarbonyl;

f') a

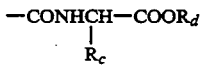

group wherein $R_d$ is hydrogen or $C_1$-$C_6$ alkyl and $R_c$ is hydrogen, phenyl or the side-chain or an α-aminoacid;

g') a

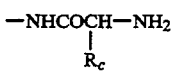

group, wherein $R_c$ is as defined above;

h') a

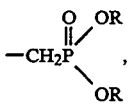

a —$CH_2OCO(CH_2)_n$COOR or a —$NHCO(CH_2)_n$COOR group, wherein n is as defined above and R is hydrogen or $C_1$-$C_6$ alkyl;

k') a —CH=N—OR'$_1$ group wherein R'$_1$ is hydrogen or a —$CH_2COOH$ group;

i') a —CH=N—NH—R'$_2$ group wherein R'$_2$ is hydrogen, —$CH_2CH_2OH$, $C_2$ or $C_3$ alkoxycarbonyl or a —$(CH_2)_p$—R'$_3$ group wherein p is 1 or 2 and R'$_3$ is COOH or $C_2$-$C_7$ alkoxycarbonyl;

l') a

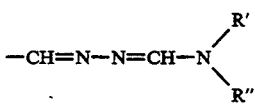

group wherein R' and R" are as defined above; or m') a

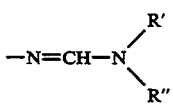

group wherein R' and R" are as defined above; or n') a $C_2$-$C_7$ alkoxycarbonyl group substituted by a

group, wherein R' and R" are as defined above; and
Q represents hydrogen, carboxy, $C_2$-$C_7$ alkoxycarbonyl or a

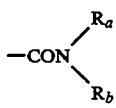

group wherein $R_a$ represents hydrogen or $C_1$-$C_{20}$ alkyl and $R_b$ represents $C_1$-$C_{20}$ alkyl, a

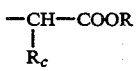

group wherein R and $R_c$ are as defined above or a —$(A)_m$—$R_5$ group wherein m is zero or 1, A is a $C_1$-$C_6$ alkylene chain and $R_5$ is a") $C_5$-$C_8$ cycloalkyl;
b") pyridyl, unsubstituted or substituted by one or two substituents chosen independently from halogen, $C_1$-$C_6$ alkyl and $C_1$-$C_6$ alkoxy;
c") phenyl, unsubstituted or substituted by one or two substituents independently chosen from halogen, $CF_3$, $C_1$-$C_6$ alkyl, $C_1$-$C_6$ alkoxy, amino, nitro, formylamino, $C_2$-$C_8$ alkanoylamino, di($C_1$-$C_6$ alkyl)amino, hydroxy, $CH_2OH$, $COOH$, $C_2$-$C_7$ alkoxycarbonyl, formyloxy, $C_2$-$C_8$ alkanoyloxy and a

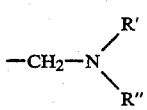

group wherein R' and R" are as defined above;
d") 2-thienyl, 2-furyl or 1-($C_1$-$C_6$ alkyl)-pyrrol-2-yl; or
e") a heterocyclic ring which is selected from 2-pyrimidyl, 2-thiazolyl and 3-isoxazolyl and which is unsubstituted or substituted by $C_1$-$C_6$ alkyl; and the pharmaceutically acceptable salts thereof.

The present invention includes within its scope all possible isomers, stereoisomers and optical isomers and their mixtures, and the metabolites and the metabolic precursors or bioprecursors of the compounds of formula (I). It has be to be noticed that the compounds of formula (I) may be represented also by a tautomeric structure, namely the enol structure of formula (Ia)

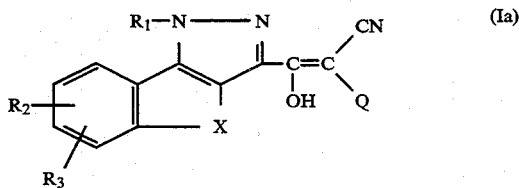

wherein

X, $R_1$, $R_2$, $R_3$ and Q are as defined above. However, the compounds of formula (Ia), which fall within the scope of the present invention too, are described in the present specification as compounds of formula (I). A halogen atom is preferably chlorine or fluorine. The alkyl, alkylene, alkanoyloxy, alkoxy and alkanoylamino groups may be branched or straight chain groups. A $C_1$-$C_{20}$ alkyl group is preferably a $C_1$-$C_6$ alkyl group. A $C_1$-$C_6$ alkyl group is e.g., methyl, ethyl, propyl, isopropyl, butyl or tert.butyl, more preferably methyl, ethyl or tert.butyl.

A $C_3$ or $C_4$ alkenyloxy group is preferably allyloxy.

A $C_1$-$C_6$ alkoxy group is, e.g., methoxy, ethoxy, propoxy, isopropoxy, butoxy or tert.butoxy, preferably it is methoxy, ethoxy or propoxy.

A $C_5$-$C_8$ cycloalkyl group is preferably cyclopentyl or cyclohexyl.

A $C_2$-$C_8$ alkanoylamino group is preferably acetylamino or propionylamino.

A $C_2$-$C_8$ alkanoyloxy group is preferably acetoxy or propionyloxy.

A $C_2$-$C_7$ alkoxycarbonyl group is preferably a $C_2$-$C_5$ alkoxycarbonyl group, in particular a $C_2$ or $C_3$ alkoxycarbonyl one.

A $C_1$-$C_6$ alkylene chain is preferably a $C_1$-$C_3$ alkylene chain, such as a —$CH_2$—, —$(CH_2)_2$—, —$(CH_2)_3$—,

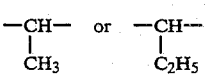

chain.

A di($C_1$-$C_6$ alkyl)amino is preferably a di($CH_1$-$C_4$ alkyl)amino group, in particular a di($C_1$ or $C_2$ alkyl)amino one. In a

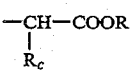

group, wherein R is as defined above and $R_c$ is as defined above except hydrogen, the asymmetric carbon atom to which —$R_c$ and —COOR are linked may have either the R or S configuration. The side-chain of an α-aminoacid is specifically the residue obtained from an α-aminoacid by removing the amino and the carboxy groups together with the α-carbon atom to which they are linked. The side-chain of an α-aminoacid as defined above is preferably the side-chain deriving from a naturally occurring aminoacid.

Examples of such aminoacids are alanine, valine, leucine, isoleucine, phenylalanine, proline, hydroxyproline, serine, threonine, cysteine, cystine, methionine, tryptophan, tyrosine, asparagine, glutamine, aspartic acid, glutamic acid, lysine, arginine, histidine and phenylserine.

Preferred examples of said chains of the above mentioned aminoacids are —$CH_3$ (deriving from alanine), —$CH_2$—$CH(CH_3)_2$ (deriving from leucine) and —$CH_2$—$C_6H_5$ (deriving from phenylalanine).

Examples of pharmaceutically acceptable salts are either those with inorganic bases such as sodium, potassium, calcium and aluminium hydroxides, or with organic bases such as lysine, arginine, N-methyl-glutamine, triethylamine, triethanolamine, dibenzylamine, methylbenzylamine, di-(2-ethyl-hexyl)-amine, piperidine, N-ethylpiperidine, N,N-diethylaminoethylamine, N-ethylmorphoine, β-phenethylamine, N-benzyl-β-phenethylamine, N-benzyl-N,N-dimethylamine and the other acceptable organic amines, as well as the salts with inorganic acids, e.g. hydrochloric, nitric, hydrobromic and sulphuric acids and with organic acids, e.g. citric, tartaric, maleic, malic, fumaric, methanesulphonic and ethanesulphonic acids. Preferred salts of the compounds of formula (I) are the sodium and the potassium salts thereof.

As stated above, the present invention also includes within its scope pharmaceutically acceptable bioprecursors (otherwise known as pro-drugs) of the compounds of formula (I), i.e. compounds which have a different formula to formula (I) above, but which nevertheless upon administration to a human being are converted directly or indirectly in vivo into a compound of formula (I).

Preferred compounds of the invention are the compounds of formula (I), wherein X is:

a''') a

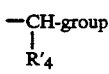
—CH-group
|
R'₄ wherein R'₄ is hydrogen, C₁–C₄ alkyl or a

—N⟨R'''/R^IV⟩ group wherein each of R''' and R^IV independently is C₁ or C₂ alkyl or R''' and R^IV, taken together with the nitrogen atom to which they are linked, form a heterocyclic ring which is selected from N-pyrrolidinyl, N-piperazinyl, morpholino and piperidino and which is unsubstituted or substituted by methyl; or b''') oxygen or a —S(O)ₙ— group, wherein n is as defined above;

R₁ represents unsubstituted pyridyl; or phenyl unsubstituted or substituted by one or two substituents chosen independently from halogen, trifluoromethyl, C₁–C₆ alkyl, C₁–C₆ alkoxy, nitro, amino and C₂–C₈ alkanoylamino;

R₂ and R₃ each independently is a⁰) hydrogen, halogen, hydroxy, COOH, CHO, CH₂OH, CF₃, C₂–C₇ alkoxycarbonyl, nitro, amino, C₁–C₄ alkyl, C₁–C₄ alkoxy or a

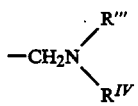
—CH₂N⟨R'''/R^IV⟩ group where R''' and R^IV are as defined above;

b⁰) a

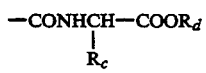
—CONHCH—COOR_d
|
R_c group wherein R_d is hydrogen or C₁–C₆ alkyl and R_c is hydrogen, phenyl or the side-chain or anα-amino-acid as defined above;

c⁰) a

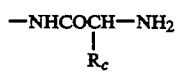
—NHCOCH—NH₂
|
R_c group, wherein R_c is as defined above;

d⁰) a —CH₂OCO(CH₂)ₙCOOR_d or a —NHCO(CH₂)ₙCOOR_d group, wherein n and R_d are as defined above;

e⁰) a —CH=N—OR'₁ group, wherein R'₁ is hydrogen or a —CH₂ COOH group;

f⁰) a

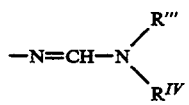
—N=CH—N⟨R'''/R^IV⟩ group wherein R''' and R^IV are as defined above;

g⁰) a C₂–C₄ alkoxycarbonyl group substituted by a

—N⟨R'''/R^IV⟩ group, wherein R''' and R^IV are as defined above;

Q represents hydrogen, C₂–C₅ alkoxycarbonyl or a —CONR'_a R'_b group wherein R'_a is hydrogen or C₁–C₆ alkyl and R'_b is C₁–C₆ alkyl, a

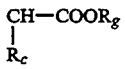
CH—COOR_g
|
R_c group wherein R_q is hydrogen or C₁–C₄ alkyl and R_c is as defined above, or a —(A')_m—R'₅ group wherein m is zero or 1, A' is a C₁–C₃ alkylene chain and R'₅ is:

a^IV) unsubstituted pyridyl; or phenyl unsubstituted or substituted by one or two substituents chosen independently from halogen, CF₃, C₁–C₄ alkyl, C₁–C₄ alkoxy, nitro, CH₂OH, COOH, di-(C₁–C₄ alkyl)amino, hydroxy, formyloxy, C₂–C₆ alkanoyloxy and a

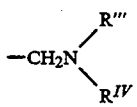
—CH₂N⟨R'''/R^IV⟩ group wherein R''' and R^IV are as defined above;

b^IV) 2-thienyl or 2-furyl; or c^IV) a heterocyclic ring which is selected from 2-thiazolyl of 3-isoxazolyl and which is unsubstituted or substituted by methyl; and the pharmaceutically acceptable salts thereof.

More preferred compounds of the invention are the compounds of formula (I) wherein X is oxygen, sulphur or a

—CH—
|
R''₄ group. wherein R''₄ is hydrogen, methyl or a

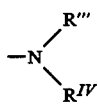
—N⟨R'''/R^IV⟩ group wherein R''' and R^IV are as defined above;

R₁ represents phenyl unsubstituted or substituted by a substituent selected from nitro, halogen, CF₃, C₁–C₄ alkyl and C₁–C₄ alkoxy; each of R₂ and R₃ independently is a^∞) hydrogen, halogen, COOH, CHO, CH₂OH, C₂–C₅ alkoxycarbonyl, CF₃, nitro, amino, hydroxy, C₁–C₄ alkyl, C₁–C₄ alkoxy, or a

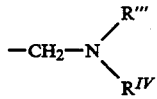
—CH₂—N⟨R'''/R^IV⟩ group wherein R''' and R^iv are as defined above;

b^∞) a

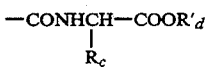

group, wherein $R'_d$ is hydrogen or $C_1$–$C_4$ alkyl and $R_c$ is as defined above;

c$^{\infty}$) a

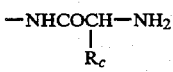

group wherein $R_c$ is as defined above:

d$^{\infty}$) a —CH$_2$OCO(CH$_2$)$_n$COOR'$_d$ or a —NHCO(CH$_2$)$_n$COOR'$_d$ group, wherein n and R'$_d$ are as defined above;

e$^{\infty}$) a

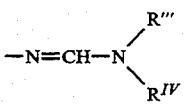

group, wherein R''' and R$^{iv}$ are as defined above;

f$^{\infty}$) a $C_2$–$C_4$ alkoxycarbonyl group substituted by a

group, wherein R''' and R$_{iv}$ are as defined above;

Q represents hydrogen, $C_2$ or $C_3$ alkoxycarbonyl or a —CONR''$_a$R''$_b$ group wherein R''$_a$ is hydrogen or $C_1$–$C_4$ alkyl and R''$_b$ is $C_1$–$C_4$ alkyl, a

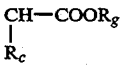

group wherein $R_g$ and $R_c$ are as defined above or a —(CH$_2$)$_p$—R''$_5$ group is which p is zero, 1 or 2 and R''$_5$ is:

a$^v$) unsubstituted pyridyl; or phenyl unsubstituted or substituted by one or two substituents chosen independently from nitro, halogen, CF$_3$, $C_1$–$C_4$ alkyl, $C_1$–$C_4$ alkoxy, CH$_2$OH, COOH, di($C_1$ or $C_2$ alkyl) amino, hydroxy, formyloxy, $C_2$–$C_6$ alkanoyloxy and a

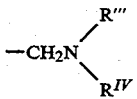

group wherein R''' and R$^{IV}$ are as defined above;

b$^v$) 2-thienyl or 2-furyl; or c$^v$) a heterocyclic ring which is selected from 2-thiazolyl or 3-isoxazolyl and which is unsubstituted or substituted by methyl; and the pharmaceutically acceptable salts thereof.

Examples of particularly preferred compounds of the invention are:

2-cyano-3-(1,4-dihydro-1-phenyl-indeno[1,2-c]pyrazol-3-yl) -3-oxo-N-phenyl-propanamide;

2-cyano-3-(7-fluoro-1,4-dihydro-1-phenyl-indeno[1,2-c]pyrazol-3-yl) -3-oxo-N-phenyl-propanamide;

2-cyano-N-(4-fluoro-phenyl)-3-[1—(4-fluoro-phenyl)-1,4-dihydro-indeno[1,2-c]pyrazol-3-yl]-3-oxo-propanamide;

2-cyano-N-(4-fluoro-phenyl)-3-(1,4-dihydro-7-methyl-1-phenyl-indeno[1,2-c]pyrazol-3-yl)-3-oxo-propanamide;

N-(3-chloro-phenyl-2-cyano-3-[1-(4-fluoro-phenyl)-1,4-dihydro-indeno[1,2-c]pyrazol-3-yl)-3-oxo-propanamide;

2-cyano-N-94-fluoro-phenyl)-3-(1,4-dihydro-1-phenyl-indeno [1,2-c]pyrazol-3-yl)-3-oxo-propanamide;

N-(3-chloro-phenyl)-2-cyano-3-(1,4-dihydro-1-phenyl-indeno [1,2-c]pyrazol-3-yl)-3-oxo-propanamide;

2-cyano-3-(1,4-dihydro-4-methyl-1-phenyl-indeno[1,2-c]pyrazol -3-yl)-3-oxo-N-phenyl-propanamide;

2-cyano-3-(1,4-dihydro-7-methyl-1-phenyl-indeno[1,2-c]pyrazol -3-yl)-3-oxo-N-phenyl-propanamide;

N-[2-cyano-3-(1,4-dihydro-1-phenyl-indeno[1,2-c]pyrazol -3-yl)-3-oxo-propanoyl]-glycine, methyl ester;

N-2-cyano-3-(1,4-dihydro-1-phenyl-indeno[1,2-c]pyrazol -3-yl)-3-oxo-propanoyl]-glycine;

2-cyano-3-oxo-3-(1-phenyl-1H-benzothieno[3,2-c]pyrazol -3-yl)-N-phenyl-propanamide;

2-cyano-N-(4-fluoro-phenyl)-3-oxo-3-(1-phenyl-1H-benzothieno [3,2-c]pyrazol-3-yl-propanamide;

2-cyano-N-(4-fluoro-phenyl)-3-[1-(4-fluoro-phenyl)-1H-benzothieno [3,2-c]pyrazol-3-yl]-3-oxo-propanamide;

2-cyano-N-(4-fluoro-phenyl)-3-(7-fluoro-1,4-dihydro-1-phenyl-indeno[1,2-c]pyrazol -3-yl)-3-oxo-propanamide; p1 3-(7-amino-1,4-dihydro-1-phenyl-indeno[1,2-c]pyrazol-3-yl)-2-cyano-3-oxo-N-phenyl-propanamide;

2-cyano-3-(5-ethoxycarbonyl-1,4-dihydro-1-phenyl-indeno[1,2-c]pyrazol-3-yl)-3-oxo-N-phenyl-propanamide;

N-[1,4-dihydro-1-phenyl-3-(2-phenylcarbamoyl-cyanoacetyl)-indeno [1,2-c]pyrazol-7-yl]carbonyl-glycine methyl ester;

2-cyano-3-(7-ethoxalylamino-1,4-dihydro-1-phenyl-indeno[1,2-c]pyrazol-3-yl)-3-oxo-N-phenyl-propanamide;

2-cyano-3-(1,4-dihydro-7-N,N-dimethylaminoethoxycarbonyl-1-phenyl -indeno[1,2-c]pyrazol-3-yl)-3-oxo-N-phenyl-propanamide;

3-(7-tert.butyl-1,4-dihydro-1-phenyl-indeno[1,2-c]pyrazol -3-yl)-2-cyano-N-(4-fluoro-phenyl)-3-oxo-propanamide;

2-cyano-N-(4-fluoro-phenyl)-3-(1,4-dihydro-1-phenyl-7-trifluoromethyl-indeno [1,2-c]pyrazol-3-yl)-3-oxo-propanamide; and the pharmaceutically acceptable salts thereof, in particular the sodium and the potassium salts.

The compounds of formula (I) and the salts thereof can be prepared by a process comprising:

a) reacting a compound of formula (II)

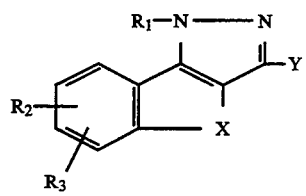

wherein

X, $R_1$, $R_2$ and $R_3$ are as defined above and Y is carboxy or a reactive derivative of a carboxy group, with a compound of formula (III)

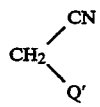

wherein

Q' is as Q defined above, except carboxy, so obtaining a compound of formula (I), wherein Q is as defined above except carboxy; or b) reacting a compound of formula (IV)

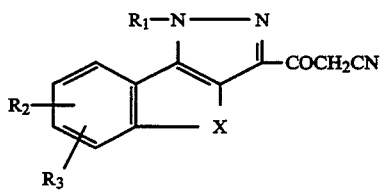

wherein

X, $R_1$, $R_2$ and $R_3$ are as defined above, with a compound formula (V)

$$R_b-N=C=O \qquad (V)$$

wherein $R_b$ is as defined above, so obtaining a compound of formula (I) wherein Q is a —$CONHR_b$ group, wherein $R_b$ is as defined above; or c) reacting a compound of formula (VI)

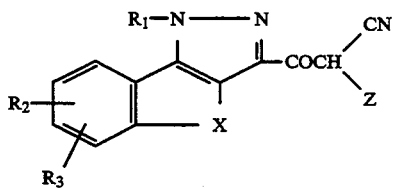

wherein

X, $R_1$, $R_2$ and $R_3$ are as defined above and Z is a reactive derivative of a carboxy group, with a compound of formula (VII)

wherein $R_a$ and $R_b$ are as defined above, so obtaining a compound of formula (I) wherein Q is a

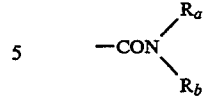

group, wherein $R_a$ and $R_b$ are as defined above; or d) hydrolysing a compound of formula (I), wherein Q is a $C_2$-$C_7$ alkoxycarbonyl or

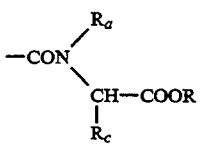

group in which $R_a$ and $R_c$ are as defined above and R is $C_1$-$C_6$ alkyl, so as to obtain the corresponding compound of formula (I), wherein Q is a free carboxy group of a

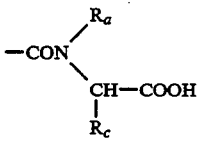

group, in which $R_a$ and $R_c$ are as defined above; and, if desired, converting a compound of formula (I) into another compound of formula (I) and/or, if desired, converting a compound of formula (I) into a pharmaceutically acceptable salt and/or, if desired, converting a salt into a free compound, and/or, if desired, separating a mixture of isomers of a compound of formula (I), into the single isomers. When Y is a reactive derivative of a carboxy group, it is, for example, a halocarbonyl group, preferably a chlorocarbonyl group, or a $C_2$-$C_7$ alkoxycarbonyl group, preferably a $C_2$-$C_3$ alkoxycarbonyl group.

The reaction between a compound of formula (II) wherein Y is carboxy and a compound of formula (III) may be carried out, for example, in the presence of a condensing agent such as diethyl cyanophgorphonate, in the presence of a base such as triethylamine, in an inert solvent such as dimethylformaide at a temperature varying between about 0° C. and about 50° C. The reaction between a compound of formula (II) wherein Y is a reactive derivative of a carboxy group and a compound of formula (III) may be carried out, for example, in the presence of a strong base such as sodium hydride, potassium t.butoxide, thallous ethoxide, in an inert solvent such as 1,2-dimethoxyethane, dioxane, dimethylformamide, at a temperature varying between about 0° C. and about 100° C.

The reaction between a compound of formula (IV) and a compound of formula (V) may be carried out, for example, in the presence of a base such as sodium hydride or triethylamine, in an inert solvent such as toluene, dioxane, tetrahydrofuran, dimethylformamide, at a temperature varying between about 0° C. and about 100° C. In the compounds of formula (VI), Z is, for example, a halocarbonyl group, preferably a chlorocarbonyl group, or a $C_2$-$C_7$ alkoxycarbonyl group, preferably a $C_2$-$C_3$ alkoxycarbonyl group.

The reaction between a compound of formula (VI), wherein Z is a halocarbonyl group, and a compound of formula (VII) may be carried out, for example, in an inert solvent such as dichloroethane, dioxane, dimethylformamide, in the presence of pyridine or triethylamine as acid acceptor, at a temperature varying between about 0° C. and about 100° C. The reaction between compound of formula (VI), wherein Z is $C_1$–$C_6$ alkyl ester, and a compound of formula (VII) may be carried out, for example, by heating at the reflux temperature in an aromatic hydrocarbon such as toluene or xylene, preferably distilling off slowly together with the diluent the free $C_1$–$C_6$ alkyl alcohol generated during the reaction.

Hydrolysis of a compound of formula (I), wherein Q is a $C_2$–$C_7$ alkoxycrbonyl group or a

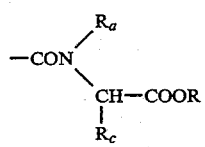

in which $R_a$ and $R_c$ are as defined above and R is $C_1$–$C_6$ alkyl, according to process—variant d) above, may be performed by selective basic hydrolysis, using e.g. aqueous sodium or potassium hydroxide in a solvent such as dioxane, ethanol or dimethylformamide at a temperature varying between about 0° C. and about 80° C.

A compound of formula (I) may be converted, as stated above, into another compound of formula (I) by known methods; for example, in a compound of formula (I) a nitro group may be converted into an amino group by treatment, for example, with stannous chloride in concentrated hydrochloric acid, using, if necessary, an organic cosolvent such as acetic acid, dioxane, tetrahydrofuran at a temperature varying between room temperature and about 100° C. Furthermore, for example, an amino group may be converted into a formylamino or a $C_2$–$C_8$ alkanoylamino group, for example by reacting with formic acid or with the suitable $C_2$–$C_8$ alkanoyl anhydride without any solvent or in an organic solvent such as dioxane, dimethylformamide, tetrahydrofuran, usually in the presence of a base such as pyridine or triethylamine, at a temperature varying between 0° C. and about 100° C. Furthermore, for example, a —$NH_2$ or a —CH=N—$NH_2$ group may be converted into a

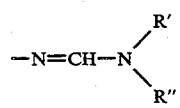

or into a

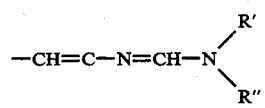

group, wherein R' and R" are as defined above, respectively, by reaction with a quaternary nitrogen compound of formula (VIIa)

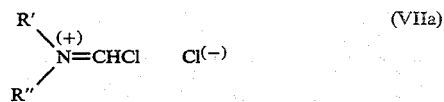

wherein R' and R" are as defined above, in an organic inert solvent, such as dioxane, tetrahydrofuran, chloroform, dichloromethane, 1,2-dichloroethane, benzene or toluene, in the presence of a tertiary amine, such as triethylamine, at a temperature varying between about −20° C. and the room temperature, according to the experimental procedure described in British patent specification 1293590 and in U.S. Pat. No. 4,447,432. Furthermore, for example, an amino group may be converted into a

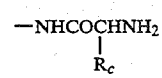

group, wherein $R_c$ is as defined above, by reaction with a suitably protected aminoacid of formula

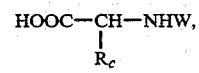

wherein $R_c$ is as defined above and W is a protective group, such as a benzyloxycarbonyl or a tert-butoxycarbonyl group, in the presence of dicyclohexylcarbodiimide, as condensing agent, in inert organic solvent such as dioxane, tetrahydrofuran or acetonitrile, at a temperature varying between about 0° C. and the room temperature, so as to obtain the protected

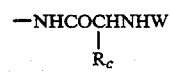

group, wherein $R_c$ and W are as defined above, which in turn is deprotected using well known methods in organic chemistry. Furthermore, for example, a carboxy group may be converted into a

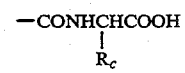

group, wherein $R_c$ is as defined above, by reaction with an esterified α-aminoacid of formula

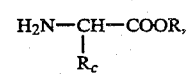

wherein R is $C_1$–$C_6$ alkyl and $R_c$ is as defined above, in the presence of dicyclohexylcarbodiimide as condensing agent, in an inert organic solvent such as dioxane, tetrhydrofuran or acetonitrile, at a temperature varying between about 0° C. and the room temperature, so as to obtain the esterified

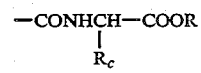

group, wherein $R_c$ and R are as defined above, which in turn is hydrolized to yield the

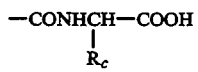

group, wherein $R_c$ is as defined above, following methods well known in the art, for example, those described for the process variant d) above. Furthermore, for example, an alkoxycarbonyl group, a

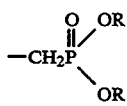

group, a —$CH_2OCO(CH_2)_nCOOR$ group or a —$NHCO(CH_2)_nCOOR$ group, wherein n is as defined above and R is $C_1$–$C_6$ alkyl, may be converted into the corresponding —COOH,

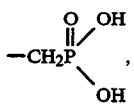

—$CH_2OCO(CH_2)_nCOOH$ and —$NHCO(CH_2)_nCOOH$ group, respectively, wherein n is as defined above, by treatment with aqueous sodium or potassium hydroxide in a solvent such as dioxane, methanol, ethanol or dimethylformamide, at a temperature varying between about 0° C. and about 80° C.

The optional esterification of a free carboxy group as well as the optional conversion of a carboxylic ester into the free carboxy derivative may be carried out according to known methods in organic chemistry.

Process-variants b) and c) described above may be considered as examples of conversion of a compound of formula (I) into another compound of formula (I) too. Also the optional salification of a compound of formula (I) as well as the conversion of a salt into the free compound and the separation of a mixture of isomers into the single isomers may be carried out by conventional methods. For example, the separation of optical isomers may be carried out by salification with an optically active base or acid and by subsequent fractional crystallization of the diastereoisomeric salts, followed by recovering of the optically active isomeric acids or, respectively, bases. The compounds of formula (II), in which Y is a $C_2$–$C_7$ alkoxycarbonyl group and X, being as defined above, is other than a

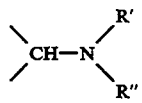

group, wherein R' and R" are as defined above, may be prepared, for example, by reacting a compound of formula (VIII)

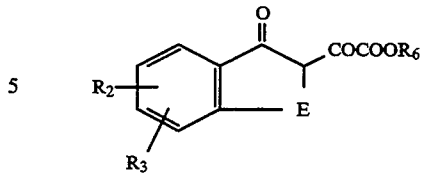 (VIII)

wherein
$R_2$ and $R_3$ are as defined above, E is as X defined above except a

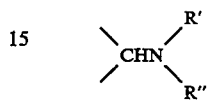

group, wherein R' and R" are as defined above, and $R_6$ is $C_1$–$C_6$ alkyl, preferably $C_1$–$C_2$ alkyl, with a compound of formula (IX)

$$R_1\text{—NHNH}_2 \qquad (IX)$$

wherein
$R_1$ is as defined above.

The reaction between a compound of formula (VIII) and a compound of formula (IX) may be carried out, for example, in a solvent such as $C_1$–$C_6$ alkyl alcohol, dioxane, tetrahydrofuran, dimethylformamide, acetic acid, at a temperature varying between about 0° C. and about 150° C. The compounds of formula (II), in which Y is a $C_2$–$C_7$ alkoxycarbonyl group and X is a

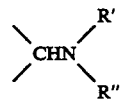

group, wherein R' and R" are as defined above, may be prepared, for example, by reacting a compound of formula (II), wherein X is >$CH_2$, with an N-halosuccinimide, preferably N-bromosuccinimide, in an inert solvent such as carbon tetrachloride or chloroform, at a temperature varying from about 20° C. to the reflux temperature, so obtaining the respective intermediate haloderivative of formula (II) in which X is a >CH-Halo group, in particular a >CHBr group, which in turn is reacted with a compound of formula

wherein R' and R" are as defined above, in a solvent such as dimethylformamide, acetone, 2-butanone, in the presence of sodium carbonate or potassium carbonate, at a temperature varying between about 0° C. and about 100° C.

The compounds of formula (II), wherein Y is carboxy may be prepared, for example, by hydrolysis of the corresponding compounds of formula (II) wherein Y is $C_2$–$C_7$ alkoxycarbonyl, according to standard methods well known in the art, for example, by basic hydrolysis, carried out e.g. by treatment with sodium or potassium hydroxide in a solvent such as water, $C_1$–$C_6$ alkyl alcohol, dioxane, dimethylformamide and their mixtures, at a temperature varying between about 0° C. and about 80° C.

The compounds of formula (II), wherein Y is halocarbonyl, preferably chlorocarbonyl, may be prepared, for example, by reaction of the corresponding compound of formula (II), wherein Y is carboxy, with the suitable acid halide, for example oxalyl chloride, thionyl chloride, $PCl_3$, $PBr_3$, in an inert solvent such as ether, benzene, dichloroethane, dioxane or without any solvent, at a temperature varying between about 0° C. and about 100° C.

The compounds of formula (III) are, in some cases, commercially available products, or may be prepared by methods well known in the art. For example a compound of formula (III), wherein Q is a

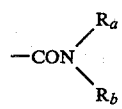

group, wherein $R_1$ and $R_b$ are as defined above, may be prepared by reacting cyano-acetic acid with a compound of formula (VII) in the presence of a condensing agent such as dicyclohexylcarbodiimide, 1,1-carbonyldiimidazole and the like, in an inert organic solvent such as benzene, dioxane, acetonitrile, at a temperature varying between about 0° C. and about 50° C.

The compounds of formula (IV) are compounds of general formula (I), wherein Q is hydrogen and may be obtained by process a) above, for example, by reacting a compound of formula (II), wherein Y is $C_2$-$C_7$ alkoxycarbonyl, with acetonitrile, in the presence of a strong base e.g. sodium hydride, potassium tert.butoxide, in an inert organic solvent such as benzene, dioxane, tetrahydrofuran, at a temperature varying between about 0° C. and about 100° C.

The compounds of formula (VI), wherein Z is $C_2$-$C_7$ alkoxycarbonyl, are compounds of general formula (I) wherein Q is $C_2$-$C_7$ alkoxycarbonyl and may be obtained by process a) above, for example, by reacting a compound of formula (II) with a compound of formula (X)

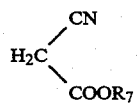

wherein
$R_7$ is $C_1$-$C_6$ alkyl, using the same experimental conditions as described above for the reaction between a compound of formula (II) and a compound of formula (III).

The compounds of formula (VI), wherein Z is halocarbonyl, may be prepared, for example, by basic hydrolysis of a compound of formula (VI), wherein Z is $C_2$-$C_7$ alkoxycarbonyl, using, for example, the same experimental conditions described above for the hydrolysis of the compounds of formula (II), wherein Y is $C_2$-$C_7$ alkoxycarbonyl, in order to obtain the corresponding carboxy derivative, which in turn may be transformed into a compound of formula (VI), wherein Z is halocarbonyl, preferably chlorocarbonyl, using, for example, the same experimental conditions described above for the preparation of the compounds of formula (II), wherein Y is halocarbonyl.

The compounds of formula (VIII) may be prepared, for example, by reacting a compound of formula (XI)

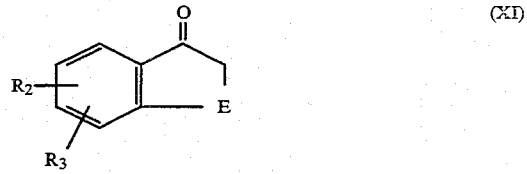

wherein
E, $R_2$ and $R_3$ are as described above, with a compound of formula (XII)

wherein
each of $R_8$ and $R_8'$, being the same or different, is $C_1$-$C_6$ alkyl, preferably methyl or ethyl.

The reaction between a compound of formula (XI) and a compound of formula (XII) may be carried out, for example, according to the methods described in J.C.S., 101, 1731 (1912) and Ann., 405, 391 (1914).

The compounds of formula (XI) may be prepared by synthetic methods well known in the art, for example, according to the methods described in J.A.C.S., 75, 1891 (1953) and Advances in Hetercocyclic Chemistry, 11, 225 (1970); ibidem 18, 432 (1975).

The compounds of formula (V), (VII), (IX), (X), and (XII) are known products and may be prepared by conventional methods: in some cases they are commercially available products.

When in the compounds of the present invention and in the intermediate products thereof, groups are present, such as CHO, COOH, $NH_2$ and/or OH, which need to be protected before submitting them to the hereabove illustrated reactions, they may be protected before the reactions take place and then deprotected, according to well known methods in organic chemistry.

The compounds of formula (I) possess immunomodulating activity and can be used for example as immunostimulant agents e.g. in the treatment of acute and chronic infections of both bacterial and viral origin, alone or in association with antibiotic agents, and in the treatment of neoplastic diseases, alone or in association with antitumoral agents, in mammals.

The immunomodulating activity of the compounds of the invention is proved, for example, by the fact that they are effective in potentiating the cytotoxic activity of the macrophages towards tumor cells in vitro.

The experimental procedure to evaluate this activity is as follows: groups of 4 mice are treated i.p. with the tested compounds and then, seven days later, peritoneal cells are collected and plated for 2 hours at 37° C. After this period the walls are washed to eliminate the non adherent cells, tumor target cells are then added and the incubation prolonged for 48 hours. At the end of this period the target cells viability is evaluated by the MTT colorimetric method (Abstracts of VIII European Immunology Meeting, Zagreb, 1987, pag 94 n°2105) based on the optical density (OD) evaluation at 570 nm.

Percent specific cytotoxicity (%C) is calculated as % inhibition of TU-5 tumor cells (Immunology, 1984, 166, 251) growth using the following formula:

$$\%C = \left(1 - \frac{(\text{effector} + \text{target})OD - \text{effector } OD}{\text{target } OD}\right) \cdot 100$$

The following Table I summarizes the immunostimulating activity data of some representative compounds of the invention, obtained according to hereabove experimental procedure, towards TU-5 tumor cells.

TABLE 1

EFFECT OF FCE 25276, FCE 25648, FCE 25651 and FCE 26047 ON THE CYTOTOXIC ACTIVITY OF PERITONEAL MACROPHAGES TOWARDS TU-5 TUMOR CELLS.

| Compound | Effector:Target | Macrophage cytotoxic activity (% inhibition of TU-5 growth) 10 mg/kg/i.p. |
|---|---|---|
| FCE 25276 | 5:1 | 93 |
| FCE 25648 | 5:1 | 77 |
| FCE 25651 | 5:1 | 79 |
| FCE 26047 | 5:1 | 82 |
| Vehicle | 5:1 | 24 |

4 animals were used for each dose.
FCE 25276 means 2-cyano-3-(1,4-dihydro-1-phenyl-indeno [1,2-c]pyrazol-3-yl)-3-oxo-N-phenyl-propanamide;
FCE 25648 means 2-cyano-3-(1,4-dihydro-1-phenyl-indeno [1,2-c]pyrazol-3-yl)-N-(4-fluoro-phenyl)-3-oxopropanamide;
FCE 25651 means N-(3-chloro-phenyl)-2-cyano-3-(1,4-dihydro-1-phenyl-indeno [1,2-c]pyrazol-3-yl)-3-oxo-propanamide;
FCE 26047 means 2-cyano-3-oxo-3-(1-phenyl-1H-benzothieno[3,2-c]pyrazol-3-yl)-N-phenyl-propanamide.

By virtue of their immunomodulatory activity the compounds of the invention proved to be active also in models of infection in mice. For example, the compounds FCE 25276, FCE 25648, FCE 25651 and FCE 26047 are strongly effective against *Pseudomonas aeruginosa* infection, performed in Cyclophosphamide immunosuppressed mice according to Cryz S. J. et al., Infect. Imm., 1983, 39, 1067.

The experimental procedure to evaluate this activity is as follows: mice are immunosuppressed 4 days before the bacterial challenge by a single dose of 200 mg/kg of Cyclophosphamide given intraperitoneally. Tested compounds are administered i.p. on days +1 and +3 relative to Cyclophosphamide administration. Clinically isolated *Pseudomonas aeruginosa* is administered intravenously in amount of 8 $LD_{50}$. Host resistance to infection is estimated by the number of mice surviving 10 days after the bacterial challenge.

The following Table 2 summarizes the obtained results.

TABLE 2

EFFECT OF FCE 25276, FCE 25648, FCE 25651 AND FCE 26047 ON *PSEUDOMONAS AERUGINOSA* INFECTION IN CYCLOPHOSPHAMIDE IMMUNODEPRESSED MICE

| Compound | treatment | % survival 8 $LD_{50}$ |
|---|---|---|
| FCE 25276 | 10 mg/kg/i.p. | 90 |
| FCE 25648 | 10 mg/kg/i.p. | 90 |
| FCE 25651 | 10 mg/kg/i.p. | 90 |
| FCE 26047 | 10 mg/kg/i.p. | 70 |
| Vehicle | — | 0 |

10 animals were used for each dose.

The compounds of the invention can be safely used in medicine by virtue of their negligible toxicity. The therapeutic regimen for the different clinical syndromes must be adapted to the type of pathology taking into account, as usual, also the route of administration, the form in which the compound is administered and the age, weight and conditions of the subject involved.

The oral route is employed, in general, for all conditions requiring such compounds. Preference is given to intravenous injection or infusion for the treatment of acute infections. For maintenance regimens the oral or parenteral, e.g. intramuscular or subcutaneous, route is preferred.

For these purposes the compounds of the invention e.g. 2-cyano-3-(1,4-dihydro-1-phenyl-indeno[1,2-]pyrazol-3-yl) -3-oxo-N-phenyl-propanamide, can be administered orally at doses ranging e.g. from about 0.5 to about 10 mg/kg of body weight per day in adult humans.

Doses of active compounds ranging e.g. from about 0.2 to about 5 mg/kg of body weight can be used for the parenteral administration in adult humans. Of course, these dosage regimens may be adjusted to provide the optimal therapeutic response.

The nature of the pharmaceutical compositions containing the compounds of this invention in association with pharmaceutically acceptable carriers or diluents will, of course, depend upon the desired route of administration. The compositions may be formulated in the conventional manner with the usual ingredients. For example, the compounds of the invention may be administered in the form of aqueous or oily solutions or suspension, tablets, pills, gelatine capsules, syrups, drops or suppositories. Thus, for oral administration, the pharmaceutical compositions containing the compounds of this invention, are preferably tablets, pills or gelatine capsules which contain the active substance together with diluents, such as lactose, dextrose, sucrose, mannitol, sorbitol, cellulose; lubricants, for instance silica, talc, stearic acid, magnesium or calcium stearate, and/or polyethylene glycols; or they may also contain binders, such as starches, gelatine, methylcellulose, carboxymethylcellulose, gum-arabic, tragacanth, polyvinylpyrrolidone, disaggregating agents, such as starches, alginic acid, alginates, sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations.

Said pharmaceutical preparations may be manufactured in known manner, for example by means of mixing, granulating, tabletting, sugar-coating, or film-coating processes.

The liquid dispersions for oral administration may be e.g. syrups, emulsions and suspensions.

The syrups may contain as carrier, for example, saccharose or saccarose with glycerine and/or mannitol and/or sorbitol. The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain together with the active compound a pharmaceutically acceptable carrier, e.g. sterile water, olive oil, ethyl oleate, glycols, e.g. propylene glycol, and if desired, a suitable amount of lidocaine hydrochloride. The solutions for intravenous injections or infusions may contain as carrier, for example, sterile water or preferably they may be in the form of sterile aqueous isotonic saline solutions.

The suppositories may contain together with the active compound a pharmaceutically acceptable carrier, e.g. cocoabutter, polyethylene glycol, a polyoxyethylene sorbitan fatty acid ester surfactant or lecithin.

The following examples illustrate but do not limit the invention:

EXAMPLE 1

2-Ethoxyalyl-indan-1-one (6 g) is reacted with phenylhydrazine (3.1 g) in acetic acid (45 ml) at 50° C. for 3 hours. After cooling the reaction mixture is diluted with ice water and then neutralized with 35% NaOH. Extraction with ethyl acetate and evaporation of the solvent in vacuo to dryness gives a residue, which is purified over a $SiO_2$ column using hexane/chloroform 6:4 as eluent. Main fractions are crystallized from isopropyl ether to yield 1,4-dihydro-1-phenyl-indeno [1,2-c] pyrazole-3-carboxylic acid, ethyl ester, m.p. 110°–112° C. (5.7 g), which is reacted with acetonitrile (14 ml) in dioxane (14 ml) in the presence of 50% sodium hydride (0.9 g) under stirring at 60° C. for 15 minutes. After cooling the reaction mixture is diluted with ice water and acidified to pH 4 with citric acid. The precipitate is filtered and purified over a $SiO_2$ column using ethyl acetate as eluent. Crystallization from dichloromethane/isopropyl alcohol gives 3-(1,4-dihydro-1-phenyl-indeno [1,2-c]pyrazol-3-yl)-3-oxo-propanenitrile, m.p. 189°–190° C. (2.8 g), which is reacted with phenyl isocyanate (1.17 g) in dimethylformamide (22 ml) in the presence of triethylamine (1.06 g) at 25°–30° C. for 25 minutes. The reaction mixture is diluted with ice water and acidified with 2N HCl to pH 3. The precipitate is filtered and washed with water. Crystallization from dichloromethane/methanol gives 3.5 g of 2-cyano-3(1,4-dihydro -1-phenyl-indeno [1,2-c]pyrazol-3-yl)-3-oxo-N-phenyl-propanamide, m.p. 273°–277° C., NMR ($CDCl_3$) α ppm: 3.91 (s) (2H, C-4 protons), 7.1–8.0 (m) (15H, phenyl protons and —CONH—), 16.2 (bs) (1H, —OH).

By proceeding analogously the following compounds can be prepared:

2-cyano-3-[1-(4-fluoro-phenyl)-1,4-dihydro-indeno[1,2-c]pyrazol-3-yl]-3-oxo-N-phenyl-propanamide;

3-1-(4-chloro-phenyl)-1,4-dihydro-indeno[1,2-c]pyrazol-3-yl]-2-cyano-3-oxo-N-phenyl-propanamide;

3-[1-(3-chloro-phenyl)-1,4-dihydro-indeno[1,2-c]pyrazol-3-yl]-2-cyano-3-oxo-N-phenyl-propanamide;

3-[1-(2-chloro-phenyl)-1,4-dihydro-indeno[1,2-c]pyrazol-3-yl]-2-cyano-3-oxo-N-phenyl-propanamide;

2-cyano-3-[1-(3-fluoro-phenyl)-1,4-dihydro-indeno[1,2-c]pyrazol-3-yl]-3-oxo-N-phenyl-propanamide;

2-cyano-3-[1,4-dihydro-1-(4-methyl-phenyl)-indeno[1,2-c]pyrazol-3-yl]-3-oxo-N-phenyl-propanamide;

2-cyano-3-[1,4-dihydro-1-(3-methyl-phenyl)-indeno[1,2-c]pyrazol-3-yl]-3-oxo-N-phenyl-propanamide;

2-cyano-3-[1,4-dihydro-1-(2-methyl-phenyl)-indeno[1,2-c]pyrazol-3-yl]-3-oxo-N-phenyl-propanamide;

2-cyano-3-[1,4-dihydro-1-(4-methoxy-phenyl)-indeno[1,2-c]pyrazol-3-yl]-3-oxo-N-phenyl-propanamide;

2-cyano-3-[1,4-dihydro-1-(3-methoxy-phenyl)-indeno[1,2-c]pyrazol-3-yl]-3-oxo-N-phenyl-propanamide;

2-cyano-3-[1,4-dihydro-1-(4-nitro-phenyl)-indeno[1,2-c]pyrazol-3-yl]-3-oxo-N-phenyl-propanamide;

2-cyano-3-[1,4-dihydro-1-(3-nitro-phenyl)-indeno[1,2-c]pyrazol-3-yl]-3-oxo-N-phenyl-propanamide; and 2-cyano-3-[1,4-dihydro-1-methyl-indeno[1,2-c]pyrazol-3-yl]-3-oxo-N-phenyl-propanamide;

EXAMPLE 2

By proceeding according to Example 1, using the suitable isocyanates, the following compounds can be prepared:

N-(3-chloro-phenyl)-2-cyano-3-(1,4-dihydro-1-phenyl-indeno[1,2-c]pyrazol-3-yl)-3-oxo-propanamide, m.p. 269°–271° C.;

N-(4-chloro-phenyl)-2-cyano-3-(1,4-dihydro-1-phenyl-indeno[1,2-c]pyrazol-3-yl)-3-oxo-propanamide;

N-(2-chloro-phenyl)-2-cyano-3-(1,4-dihydro-1-phenyl-indeno[1,2-c]pyrazol-3-yl)-3-oxo-propanamide;

2-cyano-N-(4-fluoro-phenyl)-3-(1,4-dihydro-1-phenyl-indeno[1,2-c]pyrazol-3-yl)-3-oxo-propanamide, m.p. 295°–297° C.;

2-cyano-N-(3-fluoro-phenyl)-3-(1,4-dihydro-1-phenyl-indeno[1,2-c]pyrazol-3-yl)-3-oxo-propanamide;

2-cyano-3-(1,4-dihydro-1-phenyl-indeno[1,2-c]pyrazol-3-yl)-3-oxo-N-(3-trifluoromethyl-phenyl)-propanamide, m.p. 278°–284° C.;

2-cyano-3-(1,4-dihydro-1-phenyl-indeno[1,2-c]pyrazol-3-yl)-N-(4-methyl-phenyl)-3-oxo-propanamide;

2-cyano-3-(1,4-dihydro-1-phenyl-indeno[1,2-c]pyrazol-3-yl)-N-(3-methyl-phenyl)-3-oxo-propanamide;

2-cyano-3-(1,4-dihydro-1-phenyl-indeno[1,2-c]pyrazol-3-yl)-N-(2-methyl-phenyl)-3-oxo-propanamide;

2-cyano-3-(1,4-dihydro-1-phenyl-indeno[1,2-c]pyrazol-3-yl)-N-(4-methoxy-phenyl)-3-oxo-propanamide;

2-cyano-3-(1,4-dihydro-1-phenyl-indeno[1,2-c]pyrazol-3-yl)-N-(3-methoxy-phenyl)-3-oxo-propanamide;

2-cyano-3-(1,4-dihydro-1-phenyl-indeno[1,2-c]pyrazol-3-yl)-N-(3-nitro-phenyl)-3-oxo-propanamide, m.p. 280°–284° C.;

2-cyano-3-(1,4-dihydro-1-phenyl-indeno[1,2-c]pyrazol-3-yl)-N-(4-nitro-phenyl)-3-oxo-propanamide;

N-(3-bromo-phenyl)-2-cyano-3-(1,4-dihydro-1-phenyl-indeno[1,2-c]pyrazol-3-yl)-3-oxo-propanamide;

N-benzyl-2-cyano-3-(1,4-dihydro-1-phenyl-indeno[1,2-c]pyrazol-3-yl)-3-oxo-propanamide, m.p. 289°–290° C.;

N-benzyl-2-cyano-3-[1-(4-fluoro-phenyl)-1,4-dihydro-indeno[1,2-c]pyrazol-3-yl]-3-oxo-propanamide;

2-cyano-N-(4-fluoro-phenyl)-3-[1-(4-fluoro-phenyl)-1,4-dihydro-indeno[1,2-c]pyrazol-3-yl]-3-oxo-propanamide, m.p. 281°–286° C. de N-(3-chloro-phenyl)-2-cyano-3-[1-(4-fluoro-phenyl)-1,4-dihydro-indeno[1,2-c]pyrazol-3-yl)-3-oxo-propanamide, m.p. 288°–291° C.;

N-butyl-2-cyano-3-(1,4-dihydro-1-phenyl-indeno[1,2-c]pyrazol-3-yl)-3-oxo-propanamide; and N-tert.butyl-2-cyano-3-(1,4-dihydro-1-phenyl-indeno[1,2-c]pyrazol-3-yl)-3-oxo-propanamide.

EXAMPLE 3

By proceeding according to Examples 1 and 2, starting from suitable indan-1-ones, the following compounds can be prepared:

2-cyano-3-(1,4-dihydro-4-methyl-1-phenyl-indeno[1,2-c]pyrazol-3-yl)-3-oxo-N-phenyl-propanamide;

2-cyano-3-(1,4-dihydro-5-methyl-1-phenyl-indeno[1,2-c]pyrazol-3-yl)-3-oxo-N-phenyl-propanamide;

2-cyano-3-(1,4-dihydro-6-methyl-1-phenyl-indeno[1,2-c]pyrazol-3-yl)-3-oxo-N-phenyl-propanamide;

2-cyano-3-(1,4-dihydro-7-methyl-1-phenyl-indeno[1,2-c]pyrazol-3-yl)-3-oxo-N-phenyl-propanamide, m.p. 249°–251° C.;

3-(5-chloro-1,4-dihydro-1-phenyl-indeno[1,2-c]pyrazol-3-yl)-2-cyano-3-oxo-N-phenyl-propanamide;

3-(6-chloro-1,4-dihydro-1-phenyl-indeno[1,2-c]pyrazol-3-yl)-2-cyano-3-oxo-N-phenyl-propanamide;

3-(7-chloro-1,4-dihydro-1-phenyl-indeno[1,2-c]pyrazol-3-yl)-2-cyano-3-oxo-N-phenyl-propanamide;

2-cyano-3-(7-fluoro-1,4-dihydro-1-phenyl-indeno[1,2-c]pyrazol-3-yl)-3-oxo-N-phenyl-propanamide, m.p. 259°–263° C.;

2-cyano-3-(1,4-dihydro-5-methoxy-1-phenyl-indeno[1,2-c]pyrazol-3-yl)-3-oxo-N-phenyl-propanamide;

2-cyano-3-(1,4-dihydro-7-dimethylamino-1-phenyl-indeno[1,2-c]pyrazol-3-yl)-3-oxo-N-phenyl-propanamide, 2-cyano-N-(4-fluoro-phenyl)-3-(1,4-dihydro-1-phenyl-7-trifluoromethyl-indeno[1,2-c]pyrazol-3-yl)-3-oxo-propanamide;

N-(3-chloro-phenyl)-2-cyano-3-(1,4-dihydro-1-phenyl-7-trifluoromethyl-indeno[1,2-c]pyrazol-3-yl)-3-oxo-propanamide;

N-(3-chloro-phenyl)-2-cyano-3-(7-fluoro-1,4-dihydro-1-phenyl-indeno[1,2-c]pyrazol-3-yl)-3-oxo-propanamide;

3-(7-tert.butyl-1,4-dihydro-1-phenyl-indeno[1,2-c]pyrazol-3-yl)-2-cyano-3-oxo-N-phenyl-propanamide;

3-(7-tert.butyl-1,4-dihydro-1-phenyl-indeno[1,2-c]pyrazol-3-yl)-2-cyano-N-(4-fluoro-phenyl)-3-oxo-propanamide;

2-cyano-3-(1,4-dihydro-7-morpholinomethyl-1-phenyl-indeno[1,2-c]pyrazol-3-yl)-3-oxo-N-phenyl-propanamide;

2-cyano-3-(1,4-dihydro-6-morpholinomethyl-1-phenyl-indeno[1,2-c]pyrazol-3-yl)-3-oxo-N-phenyl-propanamide;

2-cyano-3-(1,4-dihydro-5-morpholinomethyl-1-phenyl-indeno[1,2-c]pyrazol-3-yl)-3-oxo-N-phenyl-propanamide;

N-(3-chloro-phenyl)-2-cyano-3-(1,4-dihydro-7-methyl-1-phenyl-indeno[1,2-c]pyrazol-3-yl)-3-oxo-propanamide;

2-cyano-N-(4-fluoro-phenyl)-3-(1,4-dihydro-7-methyl-1-phenyl-indeno[1,2-c]pyrazol-3-yl)-3-oxo-propanamide;

2-cyano-N-(4-fluoro-phenyl)-3-(7-fluoro-1,4-dihydro-1-phenyl-indeno[1,2-c]pyrazol-3-yl)-3-oxo-propanamide; and 2-cyano-3-(1,4-dihydro-1-phenyl-7-trifluoromethyl-indeno[1,2-c]pyrazol-3-yl)-3-oxo-N-phenyl-propanamide.

EXAMPLE 4

1,4-Dihydro-1-phenyl-indeno[1,2-c]pyrazole-3-carboxylic acid, ethyl ester (7.35 g), prepared according to Example 1, is dissolved in carbon tetrachloride (100 ml) and reacted with N-bromo-succinimide (4.75 g) under stirring at the reflux temperature for 2 hours, in the presence of benzoyl peroxide (150 mg). After cooling the reaction mixture is filtered and the solution is evaporated in vacuo to a small volume. The precipitated product is purified with hot isopropyl ether to given 4-bromo-1,4-dihydro-1-phenyl-indeno [1,2-c]pyrazole-3-carboxylic acid, ethyl ester, m.p. 181°–182° C. (9.2 g) which is reacted with morpholine (2.5 g) in dimethylformamide (175 ml), in the presence of anhydrous potassium carbonate, under stirring at room temperature for 2 hours. The reaction mixture is diluted with ice water and the precipitate is filtered and washed with water until neutral. Crystallization from dichloromethane/isopropyl ether gives 1,4-dihydro-4-morpholine-1-phenyl-indeno [1,2-c]pyrazole-3-carboxylic acid, ethyl ester, m.p. 181°–182° C. (9.2 g) which is hydrolized by treatment with 1% KOH in 95% ethanol solution (93 ml) at the reflux temperature for 20 minutes. After cooling the reaction mixture is diluted in ice water and acidified with citric acid to pH 4. The precipitate is filtered, washed with water until neutral and crystallized from dichloromethane/ethanol to yield 1,4-dihydro-4-morpholino-1-phenyl-indeno [1,2-c]pyrazole-3-carboxylic acid, m.p. 244°–245° C. (4.15 g), which is reacted with thionyl chloride (1.65 ml) in dioxane (200 ml) at the reflux temperature for 1 hours. After cooling the reaction mixture is evaporated to dryness in vacuo to given 1,4-dihydro-4-morpholine-1-phenyl-indeno [1,2-c]pyrazole-3-carbonyl chloride as crystalline residue. The crude product is dissolved in anhydrous dioxane (300 ml) and reacted for 2 hours under stirring at room temperature with the carbanion obtained by treatment of 2-cyano-acetanilide (1.87 g) with 50% sodium hydride (1.2 g) in anhydrous dioxane (100 ml) at room temperature. The reaction mixture is neutralized by treatment with N HCl (7 ml) and then concentrated in vacuo to a small volume.

The residue is diluted with ice water and acidified with N HCl to pH 4. The precipitate is filtered, washed with water and then crystallized for dimethylformamide to give 2.2 g of 2-cyano-3-(1,4-dihydro-4-morpholino-1-phenyl-indeno [1,2-c]pyrazol-3-yl)-3-oxo-N-phenyl-propanamide, m.p. 272°–277° C. dec.

By processing analogously the following compounds can be prepared:

2-cyano-3-(1,4-dihydro-1-phenyl-4-piperidino-indeno[1,2-c]pyrazol-3-yl)-3-oxo-N-phenyl-propanamide;

2-cyano-3-(1,4-dihydro-1-phenyl-4-(pyrrolidin-1-yl)-indeno[1,2-c]pyrazol-3-yl)-3-oxo-N-phenyl-propanamide;

2-cyano-3-(1,4-dihydro-4-(4-methyl-piperazin-1-yl)-1-phenyl-indeno[1,2-c]pyrazol-3-yl)-3-oxo-N-phenyl-propanamide;

2-cyano-N-(4-fluoro-phenyl)-3-(1,4-dihydro-4-morpholino-1-phenyl-indeno[1,2-c]pyrazol-3-yl)-3-oxo-propanamide; and N-(3-chloro-phenyl)-2-cyano-3-(1,4-dihydro-4-morpholino-1-phenyl-indeno[1,2-c]pyrazol-3-yl)-3-oxo-propanamide.

EXAMPLE 5

1,4-Dihydro-1-phenyl-indeno[1,2-c]pyrazole-3-carboxylic acid, ethyl ester (3 g), prepared according to Example 1, is heated with 1% KOH solution in ethanol (100 ml) at reflux temperature for 20 minutes. The reaction mixture is diluted with ice water and acidified to pH 3 with 37% HCl. The precipitate is filtered, washed with water until neutral and dried in vacuo to give 1,4-dihydro-1-phenyl-indeno [1,2-c]pyrazole-3-carboxylic acid (2.5 g) which is reacted with thionyl chloride (1.2 ml) in dioxane (60 ml) at the reflux temperature for 2 hours. After cooling the reaction mixture is evaporated to dryness in vacuo to give 1,4-dihydro-1-phenyl-indeno[1,2-c]pyrazole-3-carbonyl chloride as crystalline residue. The crude product is dissolved in anhydrous dioxane (30 ml) and reacted for 2 hours under stirring at room temperature with the carbanion obtained by treatment of 2-cyano-acetanilide (1.6 g) with 50% sodium hydride (0.5 g) in anhydrous dimethylformamide/dioxane (1:1 (10 ml) at room temperature. The reaction mixture is then diluted with ice water and acidified to pH 2 with HCl. The precipitate is filtered and washed with water until neutral. Crystallization from dichloromethane/methanol gives 1.6 g of 2-cyano-3-(1,4-dihydro-1-phenyl-indeno [1,2-c]pyrazol-3-yl)-3-oxo-N-phenyl-propanamide, m.p. 273°–277° C.

By proceeding analogously the following compounds can be prepared:

2-cyano-N-(4-fluoro-benzyl)-3-(1,4-dihydro-1-phenyl-indeno [1,2-c]pyrazol-3-yl)-3-oxo-propanamide;

2-cyano-3-(1,4-dihydro-1-phenyl-indeno[1,2-c]pyrazol-3-yl) -3-oxo-N-(2-pyridyl)methyl-propanamide;

2-cyano-3-(1,4-dihydro-1-phenyl-indeno[1,2-c]pyrazol-3-yl) -3-oxo-N-(3-pyridyl)-propanamide;

2-cyano-3-(1,4-dihydro-1-phenyl-indeno[1,2-c]pyrazol-3-yl) -3-oxo-N-(2-phenethyl-propanamide;

2-cyano-3-(1,4-dihydro-1-phenyl-indeno[1,2-c]pyrazol-3-yl) -N-(4-dimethylamino-phenyl)-3-oxo-propanamide;

2-cyano-3-(1,4-dihydro-1-phenyl-indeno[1,2-c]pyrazol-3-yl) -N-(2-morpholinomethyl-benzyl)-3-oxo-propanamide;

2-cyano-3-(1,4-dihydro-1-phenyl-indeno[1,2-c]pyrazol-3-yl) -N-(3-morpholinomethyl-benzyl)-3-oxo-propanamide;

2-cyano-3-(1,4-dihydro-1-phenyl-indeno[1,2-c]pyrazol-3-yl) -N-(2-morpholinomethyl-phenyl)-3-oxo-propanamide;

2-cyano-3-(1,4-dihydro-1-phenyl-indeno[1,2-c]pyrazol-3-yl) -N-(3-morpholinomethyl-benzyl)-3-oxo-propanamide;

2-cyano-3-(1,4-dihydro-1-phenyl-indeno[1,2-c]pyrazol-3-yl) -N-(3-dimethylaminomethyl-phenyl)-3-oxo-propanamide;

2-cyano-3-(1,4-dihydro-1-phenyl-indeno[1,2-c]pyrazol-3-yl) -N-(3-hydroxy-4-hydroxymethyl-phenyl)-3-oxo-propanamide;

2-cyano-3-(1,4-dihydro-1-phenyl-indeno[1,2-c]pyrazol-3-yl) -N-(2-dimethylaminomethyl-phenyl)-3-oxo-propanamide;

2-cyano-3-(1,4-dihydro-1-phenyl-indeno[1,2-c]pyrazol-3-yl) -3-oxo-N-[2-(pyrrolidin-1-yl)methyl-phenyl]-propanamide;

2-cyano-3-(1,4-dihydro-1-phenyl-indeno[1,2-c]pyrazol-3-yl) -N-[2-(4-methyl-piperazin-1-yl)methyl-phenyl]-3-oxo-propanamide;

2-cyano-3-(1,4-dihydro-1-phenyl-indeno[1,2-c]pyrazol-3-yl) -N-(2-methoxy-3-morpholinomethyl-phenyl)-3-oxo-propanamide;

2-cyano-3-(1,4-dihydro-1-phenyl-indeno[1,2-c]pyrazol-3-yl) -N-(2-methoxy-5-morpholinomethyl-phenyl)-3-oxo-propanamide;

2-cyano-3-(1,4-dihydro-1-phenyl-indeno[1,2-c]pyrazol-3-yl) -N-methyl-3-oxo-N-phenyl-propanamide;

2-cyano-3-(1,4-dihydro-1-phenyl-indeno[1,2-c]pyrazol-3-yl) -3-oxo-N-(2-thenyl)-propanamide;

2-cyano-3-(1,4-dihydro-1-phenyl-indeno[1,2-c]pyrazol-3-yl) -N-(4-methoxy-3-morpholinomethyl-phenyl)-3-oxo-propanamide;

2-cyano-N-(2-furfuryl)-3-(1,4-dihydro-1-phenyl-indeno [1,2-c]pyrazol-3-yl)-3-oxo-propanamide;

2-cyano-3-(1,4-dihydro-1-phenyl-indeno[1,2-c]pyrazol-3-yl) -N-(1-methyl-pyrrol-2-yl)ethyl-3-oxo-propanamide;

2-cyano-3-oxo-3-(1-phenyl-1H-benzothieno[3,2-c]pyrazol-3-yl)-N-phenyl-propanamide, m.p. 288°–291° C.;

2-cyano-N-(4-fluoro-phenyl)-3-oxo-3-(1-phenyl-1H-benzothieno [3,2-c]pyrazol-3-yl)-propanamide; and N-(3-chloro-phenyl)-2-cyano-3-oxo-3-(1-phenyl-1H-benzothieno [3,2-c]pyrazol-3-yl)-propanamide;

2-cyano-N-(4-fluoro-phenyl)-3-[1-(4-fluoro-phenyl)-1H-benzothieno [3,2-c]pyrazol-3-yl]-3-oxo-propanamide.

EXAMPLE 6

Ethyl cyanoacetate (1.4 g) is treated with 50% sodium hydride (0.58 g) in anhydrous dioxane (20 ml) under stirring at room temperature until the effervescence subsides. To this solution 1,4-dihydro-1-phenyl-indeno [1,2-c]pyrazole-3-carbonyl chloride (3 g), prepared according to Example 5, dissolved in anhydrous dioxane (50 ml) is added under stirring at room temperature. The reaction mixture is allowed to react for 20 hours, then it is dilusted with ice water and acidified to pH 3 with 37% HCl. The precipitate is extracted with ethyl acetate and the organic solution washed with water and then evaporated to dryness in vacuo. The residue is purified over a SiO$_2$ column, using hexane-ethyl acetate 80:20 as eluent, to give 2-cyano-3-(1,4-dihydro-1-phenyl-indeno[1,2-c]pyrazol-3-yl) -3-oxo-propanoic acid, ethyl ester (2.2 g), which is reacted with aniline (3.4 g) in xylene (100 ml) at the reflux temperature for 48 hours. After cooling the precipitate is filtered and washed with xylene, then crystallized from dichloro-methane/methanol to give 1.2 g of 2-cyano-3-(1,4-dihydro-1-phenyl-indeno [1,2-c]pyrazol-3-yl)-3-oxo-N-phenyl-propanamide, m.p. 273°–277° C.

EXAMPLE 7

1,4-Dihydro-1-phenyl-indeno[1,2-c]pyrazole-3-carbonyl chloride (2.3 g), prepared according to Example 5, is dissolved in anhydrous dioxane (35 ml) and reacted for 2 hours under stirring at room temperature with the carbanion obtained by treatment of N-cyanoacetyl-glycine, methyl ester (1.45 g) with 50% sodium hydride (0.54 g) in anhydrous dimethylformamide/dioxane (1:1 (30 ml) at room temperature. The reaction mixture is then diluted with ice water and acidified to pH 3

The precipitate is filtered and dissolved in ethyl acetate, then the organic solution is washed with N HCl and then with water until neutral. Evaporation to dryness yields a residue which is purified over a Flash column using chloroform/methanol/30% NH$_4$OH 85:15:0.5 as eluent. Final treatment with acetone of the purified fractions gives 1.5 g of N-[2-cyano-3-(1,4-dihydro-1-phenyl-indeno[1,2-c]pyrazol-3-yl)-3-3-oxo-propanoyl]-glycine, methyl ester, m.p. 253°–255° C.

By proceeding analogously the following compounds can be prepared:

N-[2-cyano-3-(1,4-dihydro-1-phenyl-indeno[1,2-c]pyrazol-3-yl)-3-oxo-propanoyl]-DL-leucine, methyl ester;

N-[2-cyano-3-(1,4-dihydro-1-phenyl-indeno[1,2-c]pyrazol-3-yl)-3-oxo-propanoyl]-DL-phenylalanine, methyl ester;

N-[2-cyano-3-(1,4-dihydro-1-phenyl-indeno[1,2-c]pyrazol-3-yl)-3-oxo-propanoyl]-DL-phenylglycine, methyl ester; and N-[2-cyano-3-(1,4-dihydro-1-phenyl-indeno[1,2-c]pyrazol-3-yl)-3-oxo-propanoyl]-DL-isoleucine, methyl ester.

Similarly the pure D and L enantiomers of the above-listed compounds can be prepared.

EXAMPLE 8

N-[2-Cyano-3-(1,4-dihydro-1-phenyl-indeno[1,2-c]pyrazol-3-yl)-3-oxo-propanoyl]-glycine, methyl ester (1.7 g), is suspended in 1% KOH solution in 95% ethanol (60 ml) and heated under stirring at the reflux temperature for 30 minutes. After cooling the precipitate is filtered and washed with ethanol, then dissolved in water. The aqueous basic solution is extracted with ethyl acetate and then acidified to pH 3 with 2N HCl. The precipitate is extracted with ethyl acetate and the organic solution washed with N HCl and then with water until neutral. Evaporation to dryness in vacuo gives a residue which is crumbled with ethanol to yield 1.2 g of N-[2-cyano-3-(1,4-dihydro 1-phenyl-indeno[1,2-c]pyrazol-3-yl)-3-oxo-propanoyl]-glycine, m.p. 247°–249° C. dec.

By proceeding analogously the following compounds can be prepared:

N-[2-cyano-3-(1,4-dihydro-1-phenyl-indeno[1,2-c]pyrazol-3-yl)-3-oxo-propanoyl]-DL-leucine;

N-[2-cyano-3-(1,4-dihydro-1-phenyl-indeno[1,2-c]pyrazol-3-yl)-3-oxo-propanoyl]-DL-phenylalanine;

N-[2-cyano-3-(1,4-dihydro-1-phenyl-indeno[1,2-c]pyrazol-3-yl)-3-oxo-propanoyl]-DL-phenylglycine; and N-[2-cyano-3-(1,4-dihydro-1-phenyl-indeno[1,2-c]pyrazol-3-yl)-3-oxo-propanoyl]-DL-isoleucine.

Similarly the pure D and L enantiomers of the above-listed compounds can be prepared.

EXAMPLE 9

2-Cyano-3-(1,4-dihydro-1-phenyl-indeno[1,2-c]pyrazol-3-yl)-N-(3-nitro-phenyl)-3-oxo-propanamide (4.5 g) is treated with SnCl$_2$.2H$_2$O (22.5 g) in 37% HCl (16 ml) and acetic acid (144 ml) under stirring at 50° C. for 5 hours. After cooling the precipitate is filtered and washed with acetic acid, then dissolved in dimethylformamide/2N NaOH 1:1. Dilution with excess aqueous NaH$_2$PO$_4$ gives a precipitate which is filtered, washed with water and crystallized from dimethylformamide to yield 2.3 g of N-(3-amino-phenyl)-2-cyano-3-(1,4-dihydro-1-phenyl-indeno[1,2-c]pyrazol-3-yl)-3-oxo-propanamide.

By proceeding analogously the following compounds can be prepared:

N-(4-amino-phenyl)-2-cyano-3-(1,4-dihydro-1-phenyl-indeno[1,2-c]pyrazol-3-yl)-3-oxo-propanamide; and 3-[1-(4-amino-phenyl)-(1,4-dihydro-indeno[1,2-c]pyrazol-3-yl)-2-cyano-3-oxo-N-phenyl-propanamide.

EXAMPLE 10

N-(3-Amino-phenyl)-2-cyano-3-(1,4-dihydro-1-phenyl-indeno [1,2-c]pyrazol-3-yl)-3-oxo-propanamide (1.8 g) dissolved in dimethylformamide (30 ml) is reacted with acetic anhydride (5 ml) in the presence of pyridine (5 ml) at 40° C. for 8 hours. The reaction mixture is diluted with ice water and the precipitate is filtered and washed with water crystallization from dimethylformamide gives 1.2 g of N-(3-acetylamino-phenyl) -2-cyano-3-(1,4-dihydro-1-phenyl-indeno[1,2-c]pyrazol-3-yl)-3-oxo-propanamide.

By proceeding analogously the following compounds can be prepared:

N-(4-acetylamino-phenyl)-2-cyano-3-(1,4-dihydro-1-phenyl-indeno[3,2-c]pyrazol-3-yl)-3-oxo-propanamide; and 3-[1-(4-acetylamino-phenyl)-1,4-dihydro-indeno[3,2-c]pyrazol-3-yl)-3-2-cyano-3-oxo-N-phenyl-propanamide.

EXAMPLE 11

2-Cyano-3-(1,4-dihydro-1-phenyl-indeno[1,2-c]pyrazol-3-yl) -3-oxo-N-phenyl-propanamide is dissolved by treatment with the stoichiometric amount of sodium ethoxide in ethanol. The solution is evaporated to dryness in vacuo and the product is crumbled with acetone. Filtration and washing with acetone gives the pure sodium salt of 2-cyano-3-(1,4-dihydro -1-phenyl-indeno[1,2-c]pyrazol-3-yl)-3-oxo-N-phenyl-propanamide, m.p. >300° C.

By proceeding analogously the sodium salts of the following compounds can be prepared:

2-cyano-N-(4-fluoro-phenyl)-3-dihydro-1-phenyl-indeno [1,2-c]pyrazol-3-yl)-3-oxo-propanamide;

2-cyano-N-(4-fluoro-phenyl)-3-[1-(4-fluoro-phenyl)-1,4-dihydro-indeno [1,2-c]pyrazol-3-yl)-3-oxo-propanamide;

2-cyano-N-(4-fluoro-phenyl)-3-(7-fluoro-1,4-dihydro-1-phenyl-indeno [1,2-c]pyrazol-3-yl)-3-oxo-propanamide;

2-cyano-N-(4-fluoro-phenyl)-3-(1,4-dihydro-7-methyl-1-phenyl-indeno [1,2-c]pyrazol-3-yl)-3-oxo-propanamide.

EXAMPLE 12

By proceeding according to Example 5, starting from suitable tert-butoxycarbonyl-1,4-dihydro-1-phenyl-indeno[1,2-c] pyrazole-3-carboxylic acid ethyl esters, the following compound can be prepared:

3-(5-tert-butoxycarbonyl-1,4-dihydro-1-phenyl-indeno[1,2-c]pyrazol-3-yl)-2-cyano-3-oxo-N-phenyl-propanamide, m.p. 253°–255° C.;

3-(5-carboxy-1,4-dihydro-1-phenyl-indeno[1,2-c]pyrazol-3-yl)-2-cyano-3-oxo-N-phenyl-propanamide, m.p. 265°–268° C. dec;

3-(7-carboxy-1,4-dihydro-1-phenyl-indeno[1,2-c]pyrazol-3-yl)-2-cyano-N-(4-fluoro-phenyl-3-oxo-propanamide;

3-(7-carboxy-1,4-dihydro-1-phenyl-indeno[1,2-c]pyrazol-3-yl)-2-cyano-N-(3-chloro-phenyl)-3-oxo-propanamide;

3-(7-tert-butoxycarbonyl-1,4-dihydro-1-phenyl-indeno[1,2-c]pyrazol-3-yl)-2-cyano-3-oxo-N-phenyl-propanamide; and 3-(7-carboxy-1,4-dihydro-1-phenyl-indeno[1,2-c]pyrazol-3-yl)-2-cyano-3-oxo-N-phenyl-propanamide.

EXAMPLE 13

3-(5-Carboxy-1,4-dihydro-1-phenyl-indeno[1,2-c]pyrazol-3-yl)-2-cyano-3-oxo-N-phenyl-propanamide (2.3 g) dissolved in dimethylformamide (25 ml) is reacted with ethyl iodide (1.55 g) in the presence of anhydrous potassium carbonate (1.4 g) under stirring at room temperature for 2 hours. The reaction mixture is diluted with ice water and the precipitate is filtered, dissolved in chloroform and washed with 1N HCl and then with water. Evaporation of the solvent in vacuo gives a residue which is crystallized from $CH_2Cl_2$/methanol to yield 1.9 g of 2-cyano-3-(5-ethoxycarbonyl-1,4-dihydro-1-phenyl-indeno[1,2-c]pyrazol-3-yl)-3-oxo-N-phenyl-propanamide, m.p. 233°–236° C. dec.

By proceeding analogously the following compounds can be prepared:

2-cyano-3-(7-ethoxycarbonyl-1,4-dihydro-1-phenyl-indeno [1,2-c]pyrazol-3-yl)-2-cyano-3-oxo-N-phenyl-propanamide;

2-cyano-3-(7-hexyloxycarbonyl-1,4-dihydro-1-phenyl-indeno [1,2-c]pyrazol-3-yl)-3-oxo-N-phenyl-propanamide;

2-cyano-3-(7-ethoxycarbonyl-1,4-dihydro-1-phenyl-indeno [1,2-c]pyrazol-3-yl)-N-(4-fluoro-phenyl)-3-oxo-propanamide; and N-(3-chloro-phenyl)-2-cyano-3-(7-ethoxycarbonyl-1,4-dihydro-1-phenyl-indeno [1,2-c]pyrazol-3-yl)-3-oxo-propanamide.

EXAMPLE 14

Glycine methyl ester hydrochloride (0.7 g) suspended in anhydrous acetonitrile (250 ml) is treated with triethylamine (0.56 g) under stirring at room temperature. To the suspension first 3-(7-carboxy-1,4-dihydro-1-phenyl-indeno[1,2-c]pyrazole-3-yl)-2-cyano-3-oxo-N-phenyl-propanamide (2.3 g) and the dicyclohexylcarbodiimide (1.25 g) are added. The reaction mixture is kept under stirring at room temperature for 4 hours and then is basified to pH 8 by adding dimethylaminoethanol. The precipitate is filtered, washed with acetonitrile and then eliminated. The organic solution is concentrated in vacuo to a small volume, diluted with water, acidified to pH 2 with 1N HCl and then basified to pH 8 with 1N NaOH. The obtained precipitate is filtered, washed with water, dissolved in chloroform and washed with 1N HCl and then with water until neutral. The organic solution is evaporated in vacuo to dryness and the residue is purified over a $SiO_2$ column using $CHCl_3$/methanol 90/10 as eluent. Final crystallization from $CH_2Cl_2$/ethyl acetate yields 1.2 g of pure N-[1,4-dihydro-1-phenyl-3-(2-phenylcarbamoyl-cyano-acetyl)indeno[1,2-c]pyrazol-7-yl] carbonyl-glycine methyl ester.

by proceeding analogously the following compounds can be prepared.

N-[1,4-dihydro-1-phenyl-3-(2-phenylcarbamoyl-cyanoacetyl) -indeno[1,2-c]pyrazol-7-yl]carbonyl-L-alanine methyl ester;

N-[1,4-dihydro-1-phenyl-3-(2-phenylcarbamoyl-cyanoacetyl) -indeno[1,2-c]pyrazol-7-yl]carbonyl-L-leucine methyl ester;

N-[1,4-dihydro-1-phenyl-3-(2-phenylcarbamoyl-cyanoacetyl) -indeno[1,2-c]pyrazol-7-yl]carbonyl-L-phenylalanine methyl ester;

N-{3-[2-(4-fluorophenylcarbamoyl)-cyanoacetyl]-1,4-dihydro 1-phenyl-indeno[1,2-c]pyrazol-7-yl}carbonyl-glycine methyl ester; and N-[1,4-dihydro-1-phenyl-3-(2-phenylcarbamoyl-cyanoacetyl) -indeno[1,2-c]pyrazol-5-yl]carbonyl-glycine methyl ester.

EXAMPLE 15

N-[1,4-Dihydro-1-phenyl-3-(2-phenylcarbamoyl-cyanoacetyl) -indeno[1,2-c]pyrazol-7-yl]carbonyl-glycine methyl ester (0.84 g) is suspended in 1% KOH solution in 95% ethanol (22.3 ml) and heated under stirring at the reflux temperature for 30 minutes. After cooling the reaction mixture is acidified to pH 2 with 23% HCl and then diluted with ice water. The precipitate is filtered, washed with water and then crystallized from $CH_2Cl_2$/ethanol to yield 0.65 g of pure N-[1,4-dihydro-1-phenyl-3-(2-phenylcarbamoyl-cyanoacetyl) -indeno[1,2-c]pyrazol-7-yl]carbonyl glycine.

By proceeding analogously the following compounds can be prepared:

N-[1,4-dihydro-1-phenyl-3-(2-phenylcarbamoyl-cyanoacetyl) -indeno[1,2-c]pyrazol-7-yl]carbonyl-L-alanine;

N-[1,4-dihydro-1-phenyl-3-(2-phenylcarbamoyl-cyanoacetyl) -indeno[1,2-c]pyrazol-7-yl]carbonyl-L-leucine;

N-[1,4-dihydro-1-phenyl-3-(2-phenylcarbamoyl-cyanoacetyl) -indeno[1,2-c]pyrazol-7-yl]carbonyl-L-phenylalanine;

N-{3-[2-(4-fluorophenylcarbamoyl)-cyanoacetyl]-1,4-dihydro -1-phenyl-indeno[1,2-c]pyrazol-7-yl]carbonyl-glycine; and N-[1,4-dihydro-1-phenyl-3-(2-phenylcarbamoyl-cyanoacetyl) -indeno[1,2-c]pyrazol-5-yl]carbonyl-glycine.

EXAMPLE 16

6-Tosylamino-indan-1-one, m.p. 202°–204° C., (4.2 g) is reacted with diethyl oxalate (20.5 g) in anhydrous ethanol (125 ml) containing sodium ethoxide (3.75 g) under stirring in inert atmosphere at room temperature for 2 hours. The reaction mixture is diluted with ice water and extracted with hexane. The aqueous phase is acidified to pH 3 with N HCl and extracted with ethyl acetate. The organic solution is washed with water until neutral and then is evaporated to dryness in vacuo to give crude 2-ethoxalyl-6-tosylamino-indan-1-one, which is reacted with phenylhydrazine (1.65 g) in acetic acid (60 ml) at 60° C. for 2 hours. The reaction mixture is diluted with ice water and the precipitate is filtered, washed with water, dissolved in $CHCl_3$ and evaporated to dryness in vacuo. Purification over a $SiO_2$ column using hexane/ethyl acetate 7/3 as eluent yields pure 1,4-dihydro-1-phenyl-7-tosylamino -indeno[1,2- c]pyrazole-3-carboxylic acid, ethyl ester (3.3 g), which is reacted with acetonitrile (12 ml) in anhydrous dioxane (50 ml) in the presence of 50% sodium hydride (1.1 g) under stirring at 60° C. for 4 hours. After cooling the reaction mixture is diluted with ice water and acidified to pH 4 with citric acid. The precipitate is extracted with ethyl acetate, washed with 5% NaHCO3 aqueous solution and then with water. By concentration to a small volume in vacuo the product crystallizes. The precipitate is filtered and washed with ethyl acetate to yield pure 3-(1,4-dihydro-1-phenyl-7-tosylamino-indeno [1,2-c]pyrazol-3-yl)-3-oxo-propanenitrile (2.1 g), which is reacted with phenyl isocyanate (0.55 g) in dimethylformamide (15 ml) in the presence of triethylamine (0.65 ml) at room temperature for 30 minutes. The reaction mixture is diluted with ice water and acidified to pH 2 with 2N HCl.

The precipitate is filtered and washed with water until neutral. Crystallization from chloroform/ethanol yields 2-cyano-3-(1,4-dihydro-1-phenyl-7-tosylamino-indeno[1,2c]pyrazol-3-yl)-3-oxo-N-phenyl-propanamide (2.3 g), which is treated with methanesulphonic acid (11 ml) in the presence of anisole (1.3 ml) under stirring at 50° C. for 20 hours. After cooling the reaction mixture is diluted with ice water and the precipitate is filtered and washed with water until neutral. Crystallization from CH2Cl2/methanol yields 1.2 g of 3-(7-amino-1,4-dihydro-1-phenyl-indeno[1,2-c]pyrazol-3-yl)-2-cyano-3-oxo-N-phenyl-propanamide.

By proceeding analogously the following compounds can be prepared:

3-(5-amino-1,4-dihydro-1-phenyl-indeno[1,2-c]pyrazol-3-yl) -2-cyano-N-(4-fluoro-phenyl)-3-oxo-propanamide;

3-(7-amino-1,4-dihydro-1-phenyl-indeno[1,2-c]pyrazol-3-yl) -2-cyano-N-(4-fluoro-phenyl)-3-oxo-propanamide;

3-(7-amino-1,4-dihydro-1-phenyl-indeno[1,2-c]pyrazol-3-yl) -N-(3-chloro-phenyl)-2-cyano-3-oxo-propanamide; and 3-(7-amino-1,4-dihydro-1-phenyl-indeno[1,2-c]pyrazol-3-yl) -2-cyano-N-(3-trifluoromethyl-phenyl)-3-oxo-propanamide.

EXAMPLE 17

3-(7-Amino-1,4-dihydro-1-phenyl-indeno[1,2-c]pyrazol-3-yl) -2-cyano-3-oxo-N-phenyl-propanamide (1.1 g) dissolved in anhydrous dimethylformamide (70 ml) containing pyridine (1 ml) is reacted with ethyl oxalyl chloride (0.7 g) under stirring at room temperature for 6 hours. The reaction mixture is diluted with ice water and acidified to pH 4 with citric acid. The precipitate is filtered and washed with water. Crystallization from CHCl3/ethanol yields 1.1 g of 2-cyano-3-(7-ethoxalylamino -1,4-dihydro-1-phenyl-indeno[1,2-c]pyrazol-3-yl) -3-oxo-N-phenyl-propanamide.

By proceeding analogously the following compounds can be prepared:

2-cyano-3-(5-ethoxalylamino-1,4-dihydro-1-phenyl-indeno[1,2-c]pyrazol-3-yl) -3-oxo-N-phenyl-propanamide;

2-cyano-3-(7-ethoxalylamino-1,4-dihydro-1-phenyl-indeno[1,2-c]pyrazol-3-yl) -N-(4-fluoro-phenyl)-3-oxo-propanamide; and N-(3-chloro-phenyl)-2-cyano-3-(7-ethoxalylamino-1,4-dihydro -1-phenyl-indeno[1,2-c]pyrazol-3-yl)-3-oxo-propanamide.

EXAMPLE 18

2-Cyano-3-(7-ethoxalylamino-1,4-dihydro-1-phenyl-indeno[1,2-c]pyrazol-3-yl) -3-oxo-N-phenyl-propanamide (1.1 g) is treated with 1% KOH solution in 95% ethanol (34 ml) diluted with 95% ethanol (50 ml) under stirring at room temperature for 3 hours. The reaction mixture is concentrated in vacuo to a small volume and then diluted with ice water and acidified to pH 4 with citric acid. The precipitate is filtered and washed with water. Crystallization from CHCl3/ethanol yields 0.65 g of 2-cyano-3-(1,4-dihydro-7-oxalamino 1-phenyl-indeno[1,2-c]pyrazol-3-yl) -3-oxo-N-phenyl-propanamide.

By proceeding analogously the following compounds can be prepared:

2-cyano-N-(4-fluoro-phenyl)-3-1,4-dihydro-7-oxalamino -1-phenyl-indeno[1,2-c]pyrazol-3-yl)-3-oxo-propanamide;

N-3-chloro-phenyl)-2-cyano-3-1,4-dihydro-7-oxalamino -1-phenyl-indeno[1,2-c]pyrazol-3-yl)-3-oxo-propanamide; and 2-cyano-3-(1,4-dihydro-5-oxalamino-1-phenyl-indeno[1,2-c]pyrazol-3-yl) -3-oxo-N-phenyl-propanamide.

EXAMPLE 19

3-cyano-(7-Amino-1,4-dihydro-1-phenyl-indeno[1,2-c]pyrazol-3-yl) -2-cyano-3-oxo-N-phenyl-propanamide (1 g) dissolved in anhydrous tetrahydrofuran (23 ml) is reacted with succinic anhydride 0.71 g) at the reflux temperature under stirring for 3 hours. After cooling the reaction mixture is diluted with ice water. The precipitate is filtered and washed with water. Crystallization from CHCl3/methanol yields 0.75 g of 3-[7-(3-carboxy-propanoylamino-1,4-dihydro-1-phenyl-indeno[1,2-c]pyrazol-3-yl) -2-cyano-3-oxo-N-phenyl-propanamide.

By proceeding analogously the following compounds can be prepared:

3-[5-(3-carboxy-propanoylamino-1,4-dihydro-1-phenyl-indeno[1,2-c]pyrazol-3-yl) -2-cyano-3-oxo-N-phenyl-propanamide; and 3-[7-(2-carboxyacetylamino)-1,4-dihydro-1-phenyl-indeno [1,2-c]pyrazol-3-yl)-2-cyano-3-oxo-N-phenyl-propanamide.

EXAMPLE 20

5-Tert-butoxycarbonyl-1,4-dihydro-1-phenyl-indeno[1,2-c]pyrazol-3carboxylic acid ethyl ester (11 g), prepared according to Example 16, is treated under stirring with trifluoroacetic acid (130 ml) at room temperature for 3 hours. The reaction mixture is diluted with ice water and the precipitate is filtered and washed with water until neutral. Crystallization from isopropanol yields 3-ethoxycarbonyl-1,4-dihydro-1-phenyl-indeno [1,2-c]pyrazole-5-carboxylic acid (8.4 g), which is reacted with thionyl chloride (5.3 ml) in anhydrous dioxane (90 ml) at the reflux temperature for 2 hours. After cooling the solution is evaporated to dryness in vacuo and the residue, 3-ethoxycarbonyl-1,4-dihydro-1-phenyl-indeno [1,2-c]pyrazole-5-carbonyl chloride, is dissolved in anhydrous diglyme (100 ml) and added dropwise, under inert atmosphere, to a stirred solution of lithium tri-tert-butoxyaluminum hydride (15.4 g) in anhydrous diglyme (90 ml) in such as way as to maintain the temperature between 0° C. and 4° C. The reaction mixture is allowed to react at about 0° C. under stirring for 1 hour and then is diluted with ice water, acidified to pH 1 with 23% HCl and extracted with chloroform. The organic solution is washed with water and then evaporated to dryness in vacuo. The residue is purified over a SiO$_2$ column using hexane/ethyl acetate 7/3 as eluent. Crystallization from CH$_2$Cl$_2$/isopropyl ether yields pure 1,4-dihydro-5-hydroxymethyl-1-phenyl-indeno [1,2-c]pyrazole-3-carboxylic acid ethyl ester (3.8 g), which is reacted with 2-methoxyethoxymethyl chloride (2.1 g) in methylene chloride (60 ml) in the presence of diisopropylethylamine (2.96 ml) at room temperature for 20 hours. The reaction mixture is washed in a separatory funnel first with 5% Na$_2$HPO$_4$ solution and then with water until neutral. The organic phase is evaporated to dryness in vacuo and the residue is crystallized from isopropyl ether to yield 1,4-dihydro-5-(2-methoxyethoxymethoxy)methyl-1-phenyl-indeno [1,2-c]pyrazole-3-carboxylic acid ethyl ester (4.65 g), which is treated with KOH (0.4 g) in 95% ethanol (52 ml) under stirring at 45° C. for 40 minutes. The reaction mixture is then diluted with ice water and acidified to pH 4 with citric acid. The precipitate is filtered, washed with water until neutral and dried in vacuo at 80° C. to yield 1,4-dihydro-5-(2-methoxyethoxymethoxy) methyl-1-phenyl-indeno [1,2-c]pyrazole-3-carboxylic acid (3.95 g), which is dissolved in anhydrous dioxane (50 ml) and reacted with oxalyl chloride (1.9 ml) in the presence of dimethylformamide (11 mg) at room temperature for 1 hour. The reaction mixture is evaporated to dryness in vacuo and the residue, crude 1,4-dihydro-5-2-methoxyethoxymethoxy)methyl-1-phenyl-indeno[1,2-c]pyrazole -3-carbonyl chloride, is dissolved in anhydrous dioxane (50 ml) and reacted for 1 hour under stirring at room temperature with the carbanion obtained by treatment of cyano-acetanilide (1.76 g) with 50% sodium hydride (0.6 g) in anhydrous dioxane (140 ml).

The reaction mixture is then diluted with ice water and acidified to pH 3 with 2N HCl.

The precipitate is filtered, washed with water and crystallized from CH$_2$Cl$_2$/isopropanol to yield 2-cyano-3-[1,4-dihydro -(2-methoxyethoxymethoxy)methyl-1-phenyl-indeno[1,2-c]pyrazol-3-yl]-3-oxo-N-phenyl-propanamide (1.5 g), which is suspended under stirring in methanol (800 ml) containing 37% HCl (8 ml) and heated at 45° C. for 20 hours. After cooling the reaction mixture is concentrated in vacuo to a small volume and diluted with ice water. The precipitate is filtered and washed with water until neutral. Crystallization from CH$_2$Cl$_2$/methanol yields 1.05 g of 2-cyano-3-(1,4-dihydro-5-hydroxymethyl-1-phenyl -indeno[1,2-c]pyrazol-3-yl)-3-oxo-N-phenyl-propanamide.

By proceeding analogously the following compounds can be prepared:

2-cyano-3-(1,4-dihydro-7-hydroxymethyl-1-phenyl-indeno[1,2-c]pyrazol-3-yl) -3-oxo-N-phenyl-propanamide;

2-cyano-N-(4-fluoro-phenyl-3-(1,4-dihydro-5-hydroxymethyl-1-phenyl-indeno [1,2-c]pyrazol-3-yl)-3-oxo-propanamide; and N-(3-chloro-phenyl)-2-cyano-3-(1,4-dihydro-5-hydroxymethyl-1-phenyl-indeno [1,2-c]pyrazol-3-yl)-3-oxo-propanamide.

EXAMPLE 21

3-(7-carboxy-1,4-dihydro-1-phenyl-indeno[1,2-c]pyrazol-3-yl) -2-cyano-3-oxo-N-phenyl-propanamide (1.6 g) dissolved in anhydrous acetonitrile (110 ml) is reacted with N,N-dimethylaminoethanol (0.73 g), in the presence of dicyclohexylcarbodiimide (1.12 g) and 4-dimethylaminopyridine (0.265 g), under stirring at room temperature for 24 hours.

The precipitate is filtered off and the organic solution is concentrated in vacuo to a small volume. The residue is diluted with water, acidified to pH 2 with N HCl and then basified to pH 8 with N NaOH. The precipitate is filtered and purified over a SiO$_2$ column using chloroform (methanol) 30% NH$_4$OH 80/20/0.3 as eluent. The recovered product is dissolved in dimethylformamide (20 ml), acidified to pH 2 with 2N HCl, diluted with water (50 ml) and then basified to pH 8 with 2N NaOH. The precipitate is filtered and washed with water to yield 0.4 g of 2-cyano-3-(1,4-dihydro-7-N,N-dimethylamino-ethoxycarbonyl -1-phenyl-indeno[1,2-c]pyrazol-3-yl)-3-oxo-N-phenyl-propanamide.

By proceeding analogously the following compounds can be prepared:

2-cyano-3-(1,4-dihydro-5-N,N-dimethylaminoethoxycarbonyl -1-phenyl-indeno[1,2-c]pyrazol-3-yl)-3-oxo-N-phenyl-propanamide;

2-cyano-3-(1,4-dihydro-7-morpholinoethoxycarbonyl-1-phenyl-indeno[1,2-c]pyrazol-3-yl) -3-oxo-N-phenyl-propanamide; and 2-cyano-3-(7-N,N-dimethylaminopropoxycarbonyl-1,4-dihydro-1-phenyl-indeno[1,2-c]pyrazol-3-yl)-3-oxo-N-phenyl-propanamide.

EXAMPLE 22

2-cyano-3-(1,4-dihydro-5-hydroxymethyl-1-phenyl-indeno [1,2-c]pyrazol-3-yl)-3-oxo-N-phenyl-propanamide (1.1 g) is reacted with succinic anhydride (0.8 g) in anhydrous pyridine (40 ml) under stirring at 45° C. for 20 hours. After cooling the reaction mixture is diluted in ice water and the precipitate is filtered and washed with water. Crystallization from CH$_2$Cl$_2$/isopropanol yields 0.85 g of 3-[5-(3-carboxy-propanoyloxymethyl) -1,4-dihydro-1-phenyl-indeno[1,2-c]pyrazol-3-yl]-2-cyano-3-oxo-N-phenyl-propanamide.

By proceeding analogously the following compound can be prepared:

3-[7-(3-carboxy-propanoyloxymethyl)-(1,4-dihydro-7-hydroxymethyl-1-phenyl -indeno[1,2-c]pyrazol-3-yl)-2-cyano-3-oxo-N-phenyl-propanamide.

EXAMPLE 23

Tablets, each weighing 150 mg and containing 50 mg of active substance, can be manufactured as follows:

| Composition (for 10.000 tablets) | |
| --- | --- |
| 2-cyano-3-(1,4-dihydro-1-phenyl-indeno[1,2-c]pyrazol-3-yl)-3-oxo-N-phenyl-propanamide | 500 g |
| Lactose | 710 g |
| Corn starch | 238 g |
| Talc powder | 36 g |
| Magnesium stearate | 16 g |

2-cyano-3-(1,4-dihydro-1-phenyl-indeno[1,2-c]pyrazol-3-yl) -3-oxo-N-phenyl-propanamide, lactose and half of the corn starch are mixed; the mixture is then forced through a sieve of 0.5 mm openings. Corn starch (18 g) is suspended in warm water (180 ml). The resulting paste is used to granulate the powder. The granules are dried, comminuted on a sieve of sieve size 1.4 mm, then the remaining quantity of starch, talc and magnesium stearate is added, carefully mixed and processed into tablets using punches of 8 mm diameter.

By proceeding analogously, tablets can be prepared having the same composition, but containing, for example, as active substance one of the following compounds:

2-cyano-N-(4-fluoro-phenyl)-3-[1-(4-fluoro-phenyl)-(1,4-dihydro-indeno[1,2-c]pyrazol-3-yl)-3-oxo-propanamide;

2-cyano-N-(4-fluoro-phenyl)-3-(7-fluoro-1,4-dihydro-1-indeno[1,2-c]pyrazol-3-yl)-3-oxo-propanamide; and 2-cyano-N-(4-fluoro-phenyl)-3-(1,4-dihydro-7-methyl-1-phenyl-indeno[1,2-c]pyrazol-3-yl)-3-oxo-propanamide.

We claim:

1. A compound of formula (I)

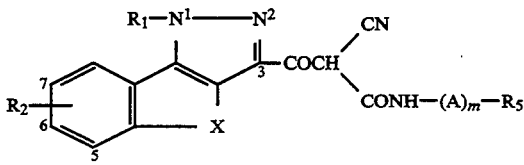

wherein

X represents:
a) a —$CH_2$— group; or
b) a sulphur atom.

$R_1$ represents a phenyl group which is unsubstituted or substituted by one or two halogen substituents;

$R_2$ is a') hydrogen, halogen, or $C_1$–$C_6$ alkyl;
b')

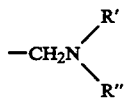

wherein R' and R", taken together with the nitrogen atom to which they are linked, form a heterocyclic ring which is selected from N-pyrrolidinyl, N-piperazinyl, thiomorpholino, morpholino and piperidino and which is unsubstituted or substituted by $C_1$–$C_6$ alkyl; or c') $C_2$–$C_7$ alkoxycarbonyl;

m is zero or 1;

A is a $C_1$–$C_6$ alkylene chain, and $R_5$ is phenyl, unsubstituted or substituted by one or two halogen substituents; and the pharmaceutically acceptable salts thereof.

2. A compound of formula (I) according to claim 1 wherein $R_2$ is a') hydrogen, halogen or $C_1$–$C_4$ alkyl;
b') —$CH_2N$ wherein —N signifies a hetercocylic ring which is selected from N-pyrrolidinyl, N-piperazinyl, thiomorpholino, morpholino and piperidino and which is unsubstituted or substituted by methyl; or
c') $C_2$–$C_7$ alkoxycarbonyl;

and the pharmaceutically acceptable salts thereof.

3. A compound of formula (I) according to claim 1 wherein A is a $C_1$–$C_3$ alkylene chain; and the pharmaceutically acceptable salts thereof.

4. A compound according to claim 1 selected from 2-cyano-3-(1,4-dihydro-1-phenyl-indeno[1,2-c]pyrazol-3-yl)-3-oxo-N-phenyl-propanamide;

2-cyano-3-(7-fluoro-1,4-dihydro-1-phenyl-indeno[1,2-c]pyrazol-3-yl)-3-oxo-N-phenyl-propanamide 2-cyano-N-(4-fluoro-phenyl)-3-[1,(4-fluoro-phenyl)-(1,4-dihydro-indeno[1,2-c]pyrazol-3-yl)-3-oxo-propanamide;

2-cyano-N-(4-fluoro-phenyl)-3-(1,4-dihydro-7-methyl-1-phenyl-indeno[1,2-c]pyrazol-3-yl)-3-oxo-propanamide;

N-(3-chloro-phenyl)-2-cyano-3-[1,(4-fluoro-phenyl)-(1,4-dihydro-indeno[1,2-c]pyrazol-3-yl)-3-oxo-propanamide;

2-cyano-N-(4-fluoro-phenyl)-3-(1,4-dihydro-1-phenyl-indeno[1,2-c]pyrazol-3-yl)-3-oxo-propanamide;

N-(3-chloro-phenyl)-2-cyano-3-(1,4-dihydro-1-phenyl-indeno[1,2-c]pyrazol-3-yl)-3-oxo-propanamide;

2-cyano-3-(1,4-dihydro-5-morpholinomethyl-1-phenyl-indeno[1,2-c]pyrazol-3-yl)-3-oxo-N-phenyl-propanamide;

3-(7-tert.butyl-(1,4-dihydro-1-phenyl-indeno[1,2-c]pyrazol-3-yl)-2-cyano-3-oxo-N-phenyl-propanamide;

2-cyano-3-(1,4-dihydro-7-methyl-1-phenyl-indeno[1,2-c]pyrazol-3-yl)-3-oxo-N-phenyl-propanamide;

2-cyano-3-oxo-3-(1H-benzothieno-3,2-c]pyrazol-3-yl)-N-phenyl-propanamide;

2-cyano-N-(4-fluoro-phenyl)-3-oxo-3-(1-phenyl-1H benzothieno[3,2-c]pyrazol-3-yl]-propanamide;

2-cyano-N-(4-fluoro-phenyl)-3-[1-(4-fluoro-phenyl)-1H-benzothieno[3,2-c]pyrazol-3-yl]-3-oxo-propanamide;

2-cyano-N-(4-fluoro-phenyl)-3-(7-fluoro-1,4-dihydro-1-phenyl-indeno[1,2-c]pyrazol-3-yl)-3-oxo-propanamide;

2-cyano-3-(5-ethoxycarbonyl-1,4-dihydro-1-phenyl-indeno[1,2-c]pyrazol-3-yl)-3-oxo-N-phenyl-propanamide;

3-(7-tert.butyl-1,4-dihydro-1phenyl-indeno[1,2-c]pyrazol-3-yl)-2-cyano-N-(4-fluoro-phenyl)-3-oxo-propanamide;

2-cyano-3-(7-fluoro-1,4-dihydro-1phenyl-indeno[1,2-c]pyrazol-3-yl)-3-oxo-N-phenyl-propanamide;

and the pharmaceutically acceptable salts thereof.

5. A pharmaceutical composition containing a pharmaceutically acceptable carrier and/or diluent and, as an active principle, a compound of formula (I) according to claim 1 or a pharmaceutically acceptable salt thereof.

6. A method of causing an immunostimulating effect in a patient in need of such effect, comprising administering to said patient an immunostimulating-effective amount of a compound of claim 1.

* * * * *